(12) United States Patent
Bhargava et al.

(10) Patent No.: US 9,230,063 B2
(45) Date of Patent: *Jan. 5, 2016

(54) AUTOMATED PROSTATE TISSUE REFERENCING FOR CANCER DETECTION AND DIAGNOSIS

(75) Inventors: Rohit Bhargava, Urbana, IL (US); Jin Tae Kwak, Champaign, IL (US); Saurabh Sinha, Champaign, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 825 days.

This patent is subject to a terminal disclaimer.

(21) Appl. No.: 13/353,196

(22) Filed: Jan. 18, 2012

(65) Prior Publication Data

US 2012/0290607 A1 Nov. 15, 2012

Related U.S. Application Data

(63) Continuation-in-part of application No. 13/344,461, filed on Jan. 5, 2012.

(60) Provisional application No. 61/429,935, filed on Jan. 5, 2011.

(51) Int. Cl.
*G06F 17/30* (2006.01)
*G06F 19/00* (2011.01)

(52) U.S. Cl.
CPC .......... *G06F 19/345* (2013.01); *G06F 19/3443* (2013.01)

(58) Field of Classification Search
CPC ... G06F 19/345; G06F 19/3443; G06F 17/30; C12Q 1/6886; C12Q 2600/158; C12Q 2600/118; C12Q 2600/112; C12Q 2600/156; C12Q 2563/107; C12Q 2600/178; C12Q 2525/207; C12Q 2600/106; C12Q 2600/136; C12Q 1/6818; G01N 33/564
USPC ............... 707/769, E17.014, E17.019; 435/6, 435/6.11, 6.12, 7.1, 7.4, 7.92, 7.9, 23, 15, 435/7.23, 91.1, 91.2, 4, 723, 29, 71, 6.14, 435/6.1; 702/19, 20; 506/8, 9, 17, 24.33, 506/24.31; 424/74.1, 277.1; 436/86, 501
See application file for complete search history.

(56) References Cited

U.S. PATENT DOCUMENTS

| | | | |
|---|---|---|---|
| 2002/0115121 A1* | 8/2002 | Garwin | ........................ 435/7.23 |
| 2004/0053247 A1* | 3/2004 | Cordon-Cardo | ... A61K 38/1709 435/6.14 |

(Continued)

OTHER PUBLICATIONS

J-M Mosquera et al.—"Morphological features of TMPRSS2—ERG gene fusion prostate cancer"—Journal of Pathology—J Pathol 2007; 212: 91-101 Published online Mar. 23, 2007 in Wiley InterScience The Journal of Pathology vol. 212, Issue 1, Article first published online; Mar. 23, 2007.*

(Continued)

*Primary Examiner* — Anh Ly
(74) *Attorney, Agent, or Firm* — Guntin & Gust, PLC; Andrew Gust

(57) ABSTRACT

This application provides to a method for identifying one or more prostate tissue samples in a database that are closest to a test prostate sample, which can be used to aid pathologists when examining prostate tissues to attain reliable and consistent diagnoses of prostate cancer. Also provided are databases and computer algorithms that can be used with such methods.

20 Claims, 19 Drawing Sheets

(56) References Cited

U.S. PATENT DOCUMENTS

| | | | |
|---|---|---|---|
| 2006/0204071 A1* | 9/2006 | Ortyn et al. | 382/133 |
| 2007/0019854 A1* | 1/2007 | Gholap et al. | 382/133 |
| 2008/0317325 A1* | 12/2008 | Ortyn et al. | 382/133 |
| 2010/0088264 A1* | 4/2010 | Teverovskiy et al. | 706/46 |
| 2010/0098306 A1* | 4/2010 | Madabhushi et al. | 382/128 |
| 2010/0177950 A1* | 7/2010 | Donovan et al. | 702/19 |
| 2010/0184093 A1* | 7/2010 | Donovan et al. | 435/7.21 |
| 2010/0317002 A1* | 12/2010 | Daniely | C12Q 1/6841 435/6.11 |
| 2012/0058901 A1* | 3/2012 | Killary et al. | 506/7 |
| 2012/0226709 A1* | 9/2012 | Bhargava et al. | 707/769 |
| 2012/0290607 A1* | 11/2012 | Bhargava et al. | 707/769 |
| 2013/0080134 A1* | 3/2013 | Donovan et al. | 703/11 |

OTHER PUBLICATIONS

Muhammad Arif and Nasir Rajpoot—"Classification of Potential Nuclei in Prostate Histology Images using Shape Manifold Learning"—Published in: Machine Vision, 2007. ICMV 2007. International Conference on Date of Conference: Dec. 28-29, 2007—pp. 113-118.*

Bhargava et al. "High Throughput Assessment of Cells and Tissues: Bayesian Classification of Spectral Metrics from Infrared Vibrational Spectroscopic Imaging Data," *Biochimica Et Biophysica Acta* 1758:830-845, 2006.

Cintra and Billis, "Histologic Grading of Prostatic Adenocarcinoma: Intraobserver Reproducibility of the Mostofi, Gleason, and Böcking Grading Systems," *Int. Urol. Nephrol.* 23:449-454, 1991.

Egevad, et al., "Current Practice of Gleason Grading Amoung Genitourinary Pathologists," *Hum. Pathol.* 36:5-9, 2005.

Geary, R. C., "The Contiguity Ratio and Statistical Mapping," *The Incorporated Statistician* 5:115-146, 1954.

Hamden et al., "Should the Gleason Grading System for Prostate Cancer be Modified to Account for High-Grade Tertiary Components? A Systematic Reveiw and Meta-Analysis," *Lancet Oncol.* 8:411-419, 2007.

Joachims, "Training Linear SVMs in Linear Time," Proceedings of the 12th ACM SIGKDD international conference on Knowledge discovery and data mining 2006, pp. 217-226.

Moran, P.A.P., "Notes on Continuous Stochastic Phenomena," *Biometrika* 37:17-23, 1950.

Smith, et al., "Similarity Measurement Method for the Classification of Architecturally Differentiated Images," *Comput. Biomed. Res.* 32:1-12, 1999.

Stotzka et al., "A Hybrid Neural and Statisical Classifier System for Histopathologic Grading Prostatic Lesions," *Anal. Quant. Cytol. Histol.* 17:204-218, 1995.

Sved, et al., "Limitations of Biopsy Gleason Grade: Implications for Counseling Patients with Biopsy Gleason Score 6 Prostate Cancer," *J. Urol.* 172:98-102, 2004.

* cited by examiner

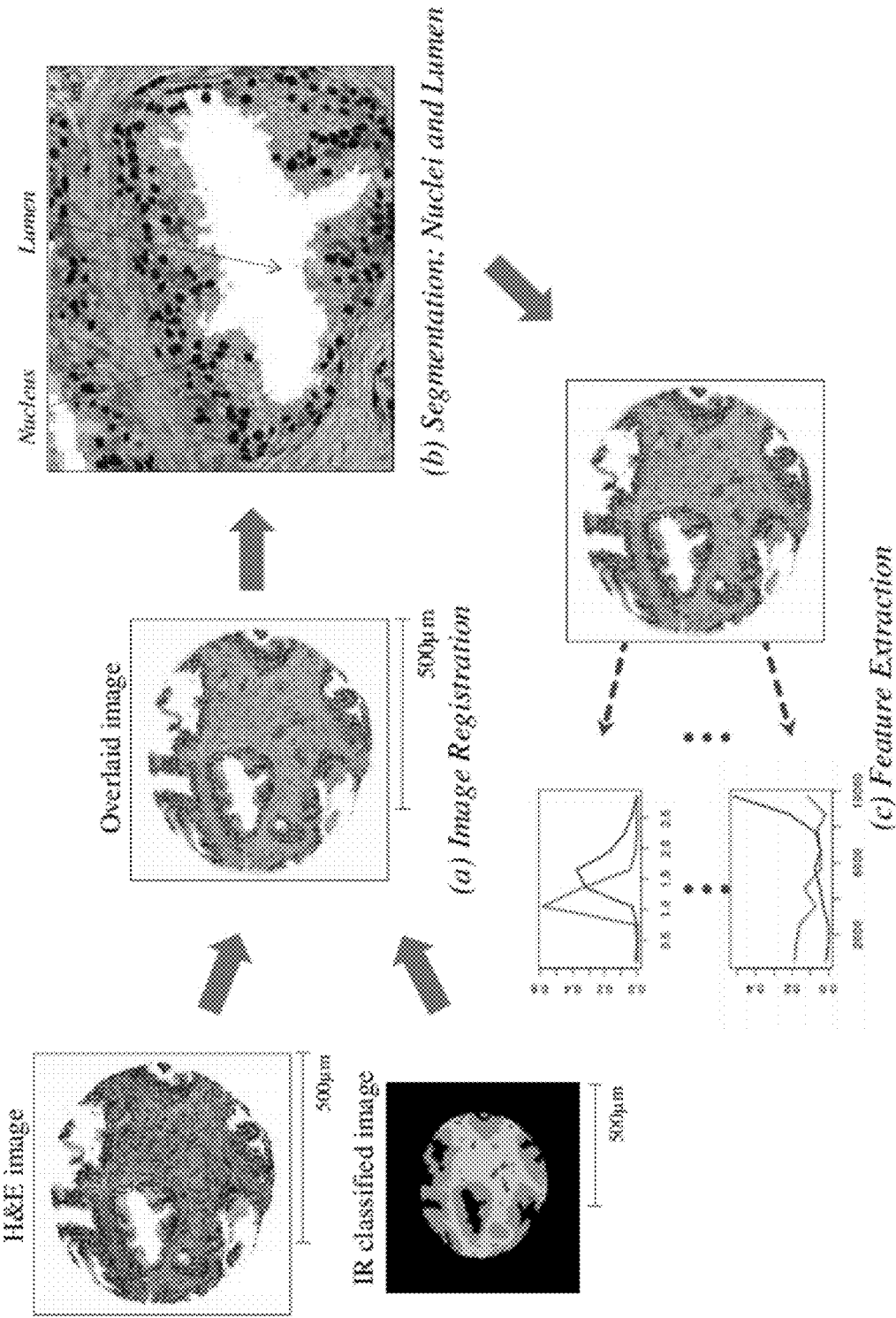

AUTOMATED PROSTATE TISSUE REFERENCING FOR CANCER DETECTION AND DIAGNOSIS

CROSS REFERENCE TO RELATED APPLICATION

This application is a continuation-in-part of co-pending U.S. application Ser. No. 13/344,461 filed Jan. 5, 2012, which claims priority to U.S. Provisional Application No. 61/429,935, filed Jan. 5, 2011, herein incorporated by reference.

ACKNOWLEDGMENT OF GOVERNMENT SUPPORT

This invention was made with government support under W81XWH-07-1-0242 awarded by the Department of Defense and R01CA138882 awarded by the National Institutes of Health. The government has certain rights in the invention.

FIELD

This application relates to a method to aid pathologists when examining prostate tissues to attain reliable and consistent diagnoses of prostate cancer, as well as databases and computer software that can be used with such methods.

BACKGROUND

Quality assurance in clinical pathology plays a critical role in the management of patients with prostate cancer, as pathology is the gold standard of diagnosis and forms a cornerstone of patient therapy. Methods to integrate quality development, quality maintenance, and quality improvement to ensure accurate and consistent test results are, hence, critical to cancer management. These factors have a direct bearing on patient outcomes, financial aspects of disease management as well as malpractice concerns. One of the major failings in prostate pathology today is the rate of missed tumors and variability in grading. It is well known that the grading of prostate tissues suffers from intra- and inter-pathologist variability [1]. In the studies of intra- and inter-pathologist reproducibility [2, 3], the exact intra-pathologist agreement was achieved in 43-78% of the instances, and in 36-81% of the instances, the exact inter-pathologist agreement was reported. It is also known that the variability of the grading could be reduced after pathologists are re-trained. There could be many ways to educate pathologists such as meetings, courses, online tutorials, etc. [4], but these are not time- and cost-effective for routine everyday decisions. Therefore, building an automated, fast, and objective method to aid pathologists to examine prostate tissues will greatly help to attain reliable and consistent diagnoses.

Several automated systems for the grading of prostate tissues have been developed [5-14]. The majority of systems use texture and/or morphological features to characterize and classify tissue samples into correct classes. However, the information which pathologists obtain by using such methods is limited since these only provide the predicted grade in general. The prediction also relies on the training data. These prior efforts always sought to match a sample completely to provide a diagnosis, rather than provide matching candidates. Further, the role of other modalities in the process was not clear.

SUMMARY

Provided herein are methods of identifying one or more prostate tissue samples present in a database that are the closest match to a test prostate sample. Tissue samples which have the same grade or similar morphologic or chemical characteristics or patterns, with the test sample, will afford more information to pathologists. Thus, the method enables matching to a database rather than seeking to provide an unequivocal diagnosis.

In particular examples, the method includes extracting morphological features from the test prostate tissue sample, such as the nuclear and cellular morphology of epithelial and stromal cells and lumens. Exemplary morphological feature categories include, but are not limited to those related to the epithelial cells and their nuclei (such as 1) Size of epithelial cells 2) Size of a nucleus 3) Number of nuclei 4) Distance to lumen 5) Distance to epithelial cell boundary 6) Number of isolated nuclei 7) Fraction of distant nuclei and 8) Entropy of nuclei spatial distribution), those related to the lumen (such as 1) Size of a lumen 2) Number of lumens 3) Lumen roundness 4) lumen distortion 5) Lumen minimum bounding circle ratio 6) Lumen convex hull ratio 7) Symmetric index of lumen boundary 8) Symmetric index of lumen area and 9) Spatial association of lumens and cytoplasm-rich regions), as well as other quantities describing characteristics of epithelium, stroma, lumens, and glands (such as 1) Number of stroma cells 2) Minimum lumen distance 3) Minimum gland distance 4) Ratio of lumen to epithelial cells 5) Ratio of epithelial cells to stroma cells 6) Ratio of cell separation 7) Ratio of sheets of cells 8) Degree of cell dispersion and 9) Spatial autocorrelation of cells). In one example, the morphological features extracted include at least 5, at least 10, or at least 20 of these, such as at least 5, at least 10, or at least 20, at least 30, at least 40 at least 50, at least 60, or all 67 of the features in Table 1. In one example, the morphological features extracted include at least 5, at least 10, or at least 20 of these, such as at least 5, at least 10, or at least 20, at least 30, at least 40 at least 50, at least 60, at least 100, at least 200, at least 250, at least 300, or all 308 of the features in Table 4.

The morphological feature similarities between the test prostate sample and the prostate tissue samples in a database are determined, for example using Euclidean distance and ranking algorithm (such as Ranking-SVM). Although the database may contain information for numerous morphological features for each sample in the database, not all of the features need to be compared to the morphological features extracted from the test sample. Instead, a subset of all of the morphological features extracted can be used. For example, the method can include examining all of the morphological features in the database, and a subset selected to use on the test sample. In one example, the method includes ordering the morphological features by their individual retrieval performance, and sequentially, the retrieval performance of a feature set measured by adding a new feature at a time according to the order. The morphological feature selection continues with the morphological feature set resulting the best performance in the first stage as the starting point, following the sequential floating forward selection (SFFS) method.

One or more prostate tissue samples in the database that are the most similar to the test prostate tissue sample are then retrieved from the database, for example the k prostate tissue samples in the database having the greatest similarity to the test prostate tissue sample (wherein k is the number of samples received from the database). The retrieved samples can be outputted to a user, for example by display on a screen.

One or more of the steps of the method can be performed on a suitably programmed computer.

A pathologist can then compare the retrieved tissue samples from the database, which have a confirmed pathological status (e.g., normal prostate tissue, BPH, cancerous, Gleason grade 2, 3, 4, or 5 prostate cancer), to the test prostate sample, to assist the pathologist in making a diagnosis of the test prostate sample.

The test samples and the samples in the database may include H&E stained images, IR classified images, or both. Such samples can be obtained from the prostate of a human or mammalian veterinary subject.

Databases that include a plurality of prostate tissue samples (such as known normal prostate tissue samples, cancerous prostate samples, BPH tissue samples, or combinations thereof), which can be used with the disclosed methods, are provided herein. Such databases may include images of the samples, as well as morphological feature data and clinical information, for each sample in the database.

The disclosure also provides a computer-readable storage medium having instructions thereon for performing the disclosed methods of identifying one or more prostate tissue samples in a database that are closest to a test prostate sample.

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 shows an exemplary method for extracting morphological features from a prostate tissue sample from which an H&E image and an IR image have been obtained.

where $N_S$ and $N_{SS}$ denote the number of samples in the database and the number of samples whose TMS with the query ≥$th_s$, respectively.

Figure 19:
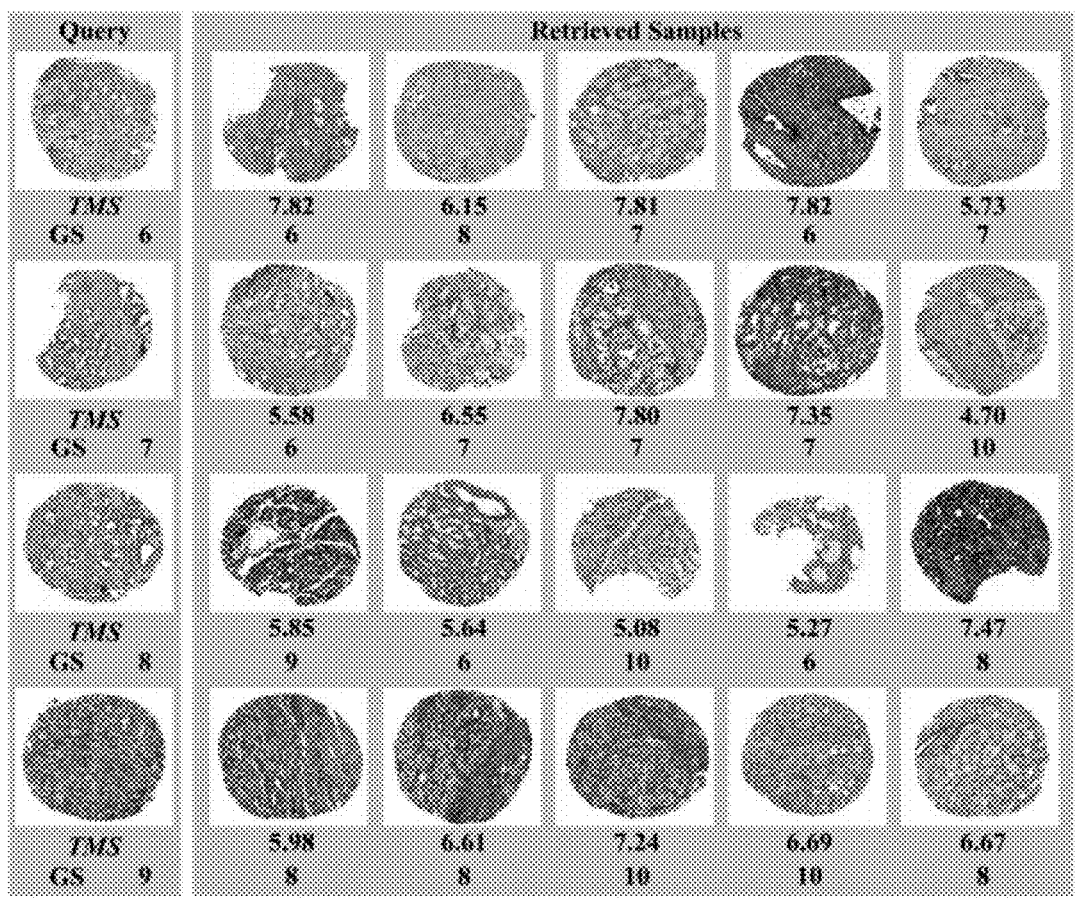

FIG. 19 is a digital image showing examples of queries and their matching cases. TMS denotes tissue morphologic similarity score for a pair of samples. GS indicates a sum of predominant and secondary Gleason scores.

Figure 20A:
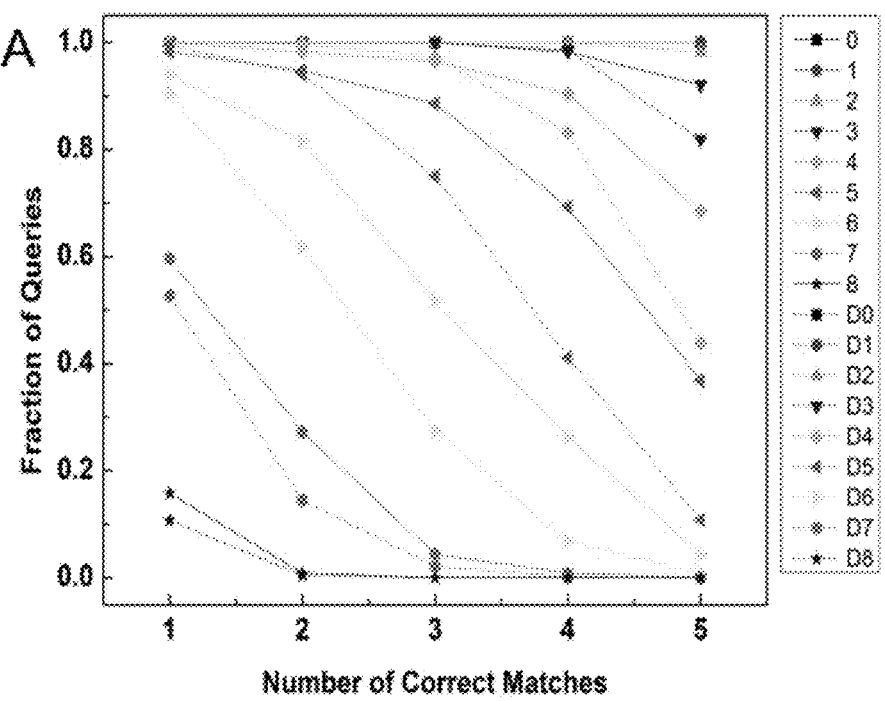
Figure 20B:
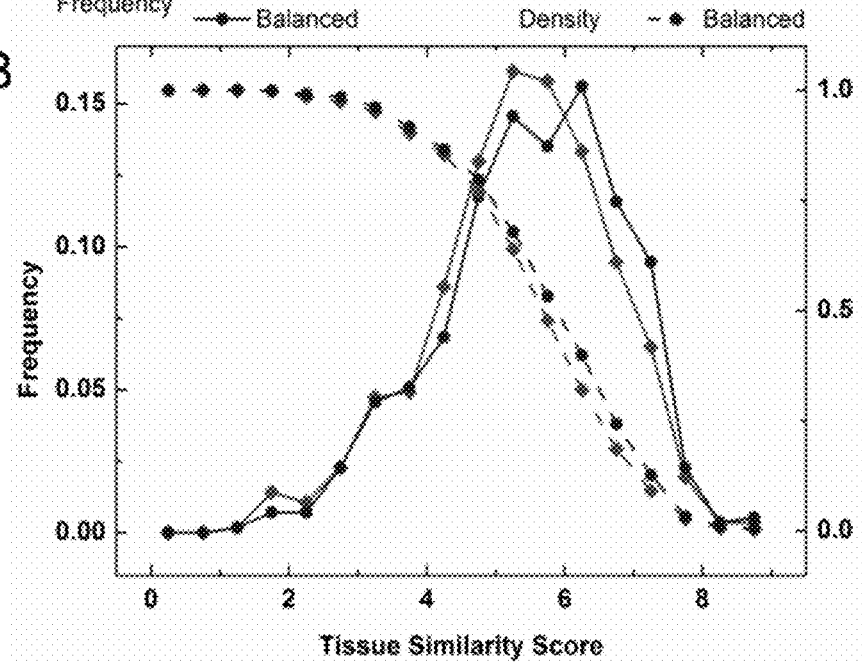

FIGS. 20A and 20B are graphs showing queries retrieving good matching cases without balanced training. (A) The number of queries retrieving at least $N_G$ number of good matches, out of T retrieved samples, is computed ($N_G$=1, ..., T), and compared to the random chance (R0~R9) of retrieving that number of good matching cases. (B) The frequency and cumulative density of similarity scores are plotted as retrieval process is trained on balanced training dataset and unbalanced training dataset, respectively. A good matching case is defined as a pair of samples whose similarity score is ≥$th_s$, $th_s$=0, ..., 8. Random chance of retrieving ≥$N_G$ good matching cases is computed as $$Pr(X \geq N_G) = \sum\nolimits_{x \geq N_G} \frac{\binom{N_{SS}}{x}\binom{N_S - N_{SS}}{T-x}}{\binom{m}{T}}$$

where $N_S$ and $N_{SS}$, denote the number of samples in the database and the number of samples whose TMS with the query ≥$th_s$ respectively.

DETAILED DESCRIPTION

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including"; hence, "comprising A or B" means "including A" or "including B" or "including A and B." All references cited herein are incorporated by reference.

Cancer: Malignant neoplasm, for example one that has undergone characteristic anaplasia with loss of differentiation, increased rate of growth, invasion of surrounding tissue, and is capable of metastasis.

Database: A compilation or storage system that includes information, such as information on a plurality of prostate samples.

Normal cells or tissue: Non-tumor, non-malignant cells and tissue.

Prostate Cancer: A malignant tumor, generally of glandular origin, of the prostate. Prostate cancers include adenocarcinomas and small cell carcinomas. Many prostate cancers express prostate specific antigen (PSA).

Subject: Includes any multi-cellular vertebrate organism, such as human and non-human mammals (e.g., veterinary subjects). In some examples, a subject is one who has cancer, or is suspected of having cancer, such as prostate cancer.

Test sample: A biological sample to be analyzed, for example a prostate sample obtained from a patient suspected of having prostate cancer.

Suitable methods and materials for the practice and/or testing of embodiments of the disclosure are described below. Such methods and materials are illustrative only and are not intended to be limiting. Other methods and materials similar or equivalent to those described herein also can be used. For example, conventional methods well known in the art to which a disclosed invention pertains are described in various general and more specific references.

Methods of Identifying Similar Samples from a Database

Herein disclosed is a computer information and management and decision-making method that relies on one or more measures of the structure of tissue to provide images from a database that are similar to the sample under consideration. The disclosed system does not provide a diagnosis but instead provides the closest matching cases in the database that enable a pathologist to make a diagnosis.

When a pathologist examines tissue, they look at a stained image of tissue and mentally compare it against a database of previous knowledge or information in books. In essence, the pathologist is manually matching structural patterns they have seen earlier and mentally recall the diagnosis made such that they can make the same diagnosis in the specific test case. Although the pathologist is well-trained and thoroughly examines the case, the decision may be in doubt due to the variability in grading. To aid and improve the diagnostic process, several automated systems for the detection and grading of prostate cancer were developed. The majority of the previous methods have used morphological features [5], [10], [11], [12], [13], [15], [16] to characterize and classify tissue samples into correct classes, and others have also used Fourier Transform [7], Wavelet Transform [13], [17], [18], and Fractal Analysis [13], [14] to extract texture features. Though previous methods claim to be accurate, the information which pathologists obtain by using such methods is limited since these only provide the predicted grade or status of tissue in general. The prediction also relies on the conditions of the training and testing datasets such as acquisition settings [10], [19] and staining [19]. Moreover, the gold standard of the previous systems was mostly Gleason grade of tissue. Due to variability in grading and the heterogeneous nature of cancer, tissues belonging to the same Gleason grade may possess different cellular, nuclear, or glandular sub-patterns. For these reasons, the sustainability of Gleason grading is in question [20] to [22]. Accordingly, a system built on Gleason grade is likely to malfunction in clinical practice. To this end, an alternative method is needed to provide comprehensive information of the test case to pathologists and to train and evaluate the automated system in an effective, rigorous, and robust way.

Figure 7:
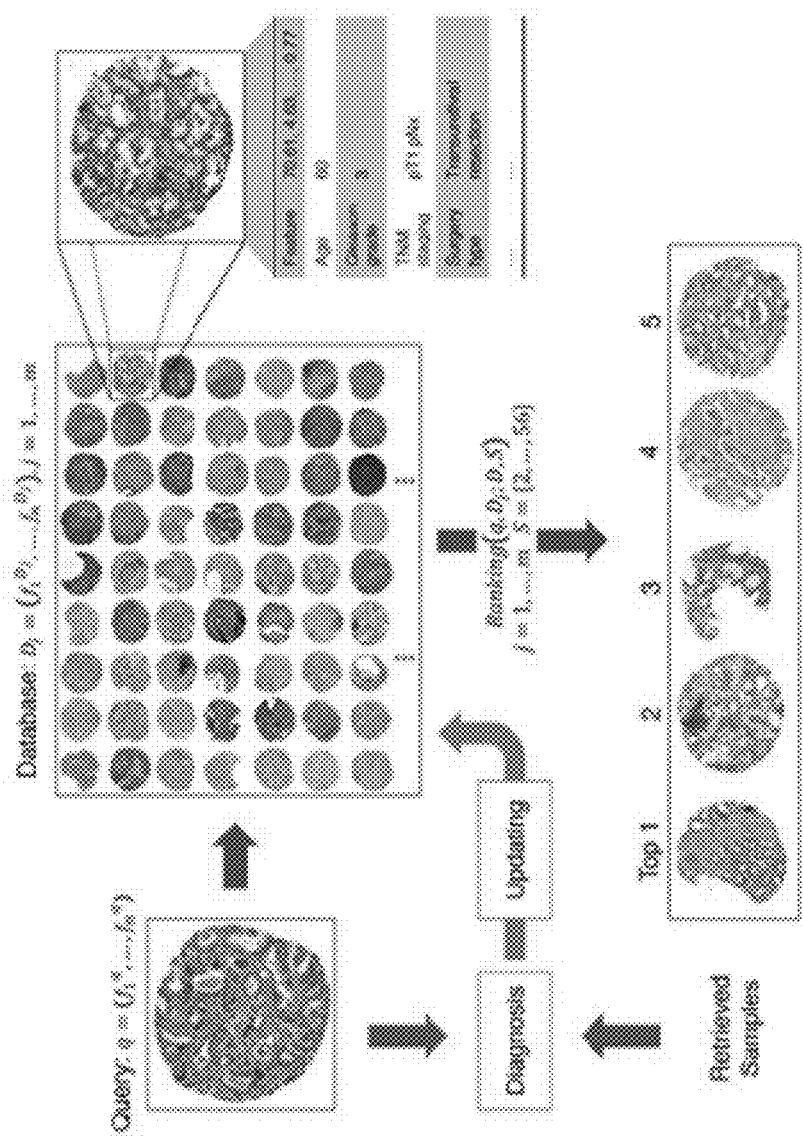
FIG. 7 provides an overview of the disclosed methods. The query (test sample) is provided, and then the closest matches and their clinical information are retrieved from the database (red arrows). Provided with the matching cases, pathologists make a diagnosis (blue arrows), and updating may or may not be conducted (green arrow). Q, D, Ranking, f, and S denote a query, database, retrieval process, single feature, and subset of features, respectively.
Figure 8:
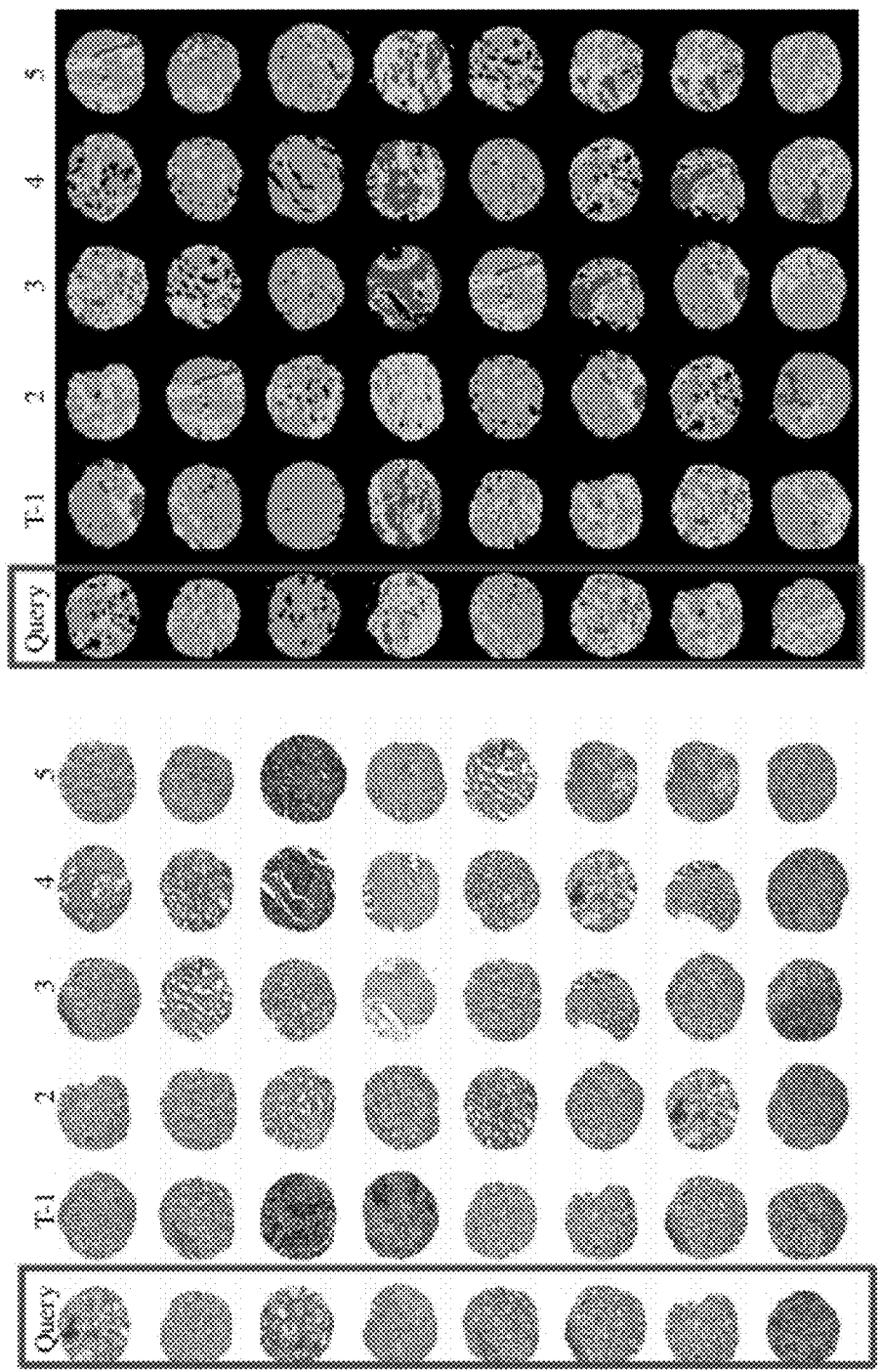
FIGS. 8-12 are digital images showing matching of a test prostate sample (column marked query) and the corresponding prostate tissue images from the database that were retrieved using the disclosed methods, for prostate cancer Gleason grade 3, 4, 5, BPH, and normal, respectively.
Figure 9:
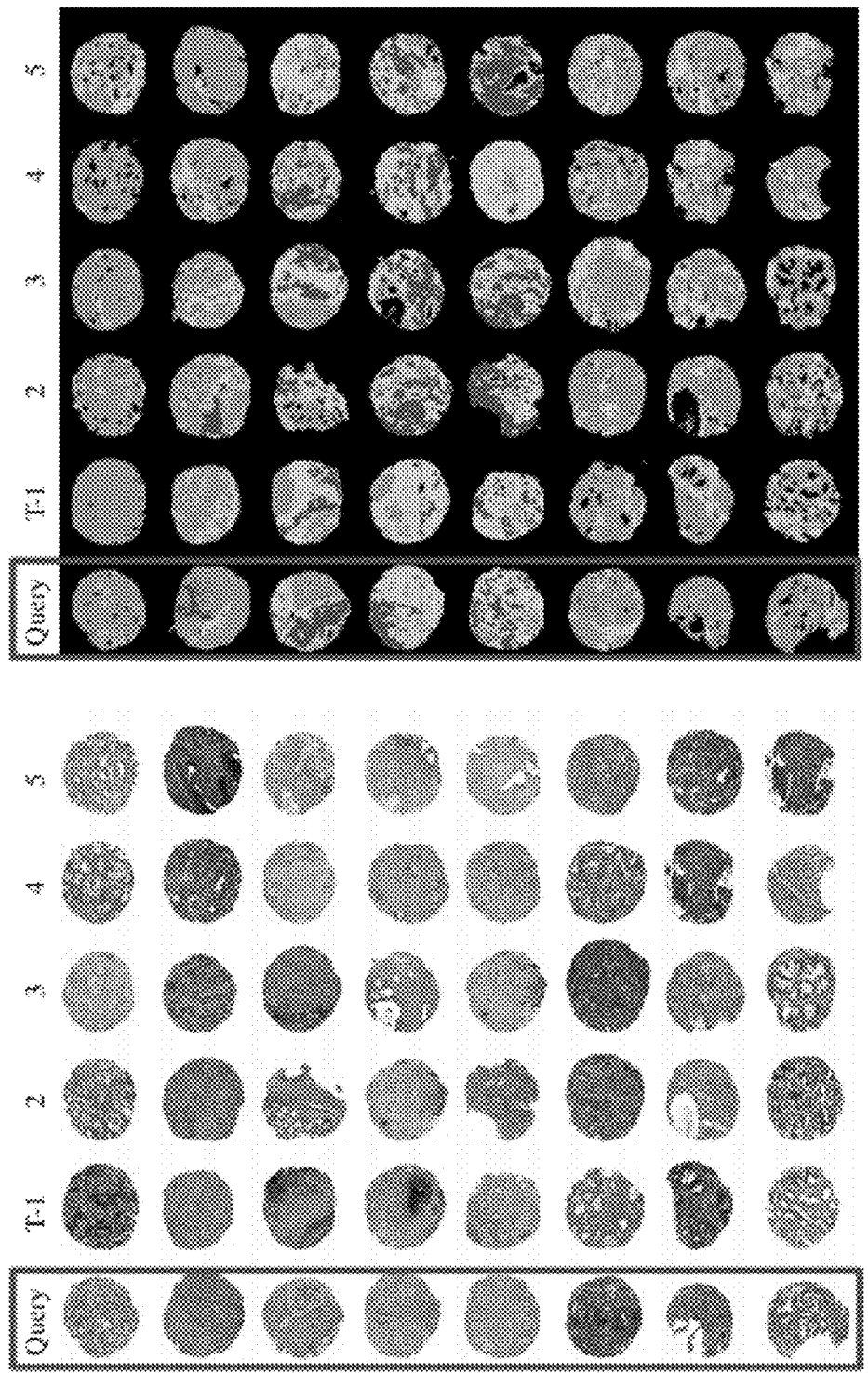
Figure 10:
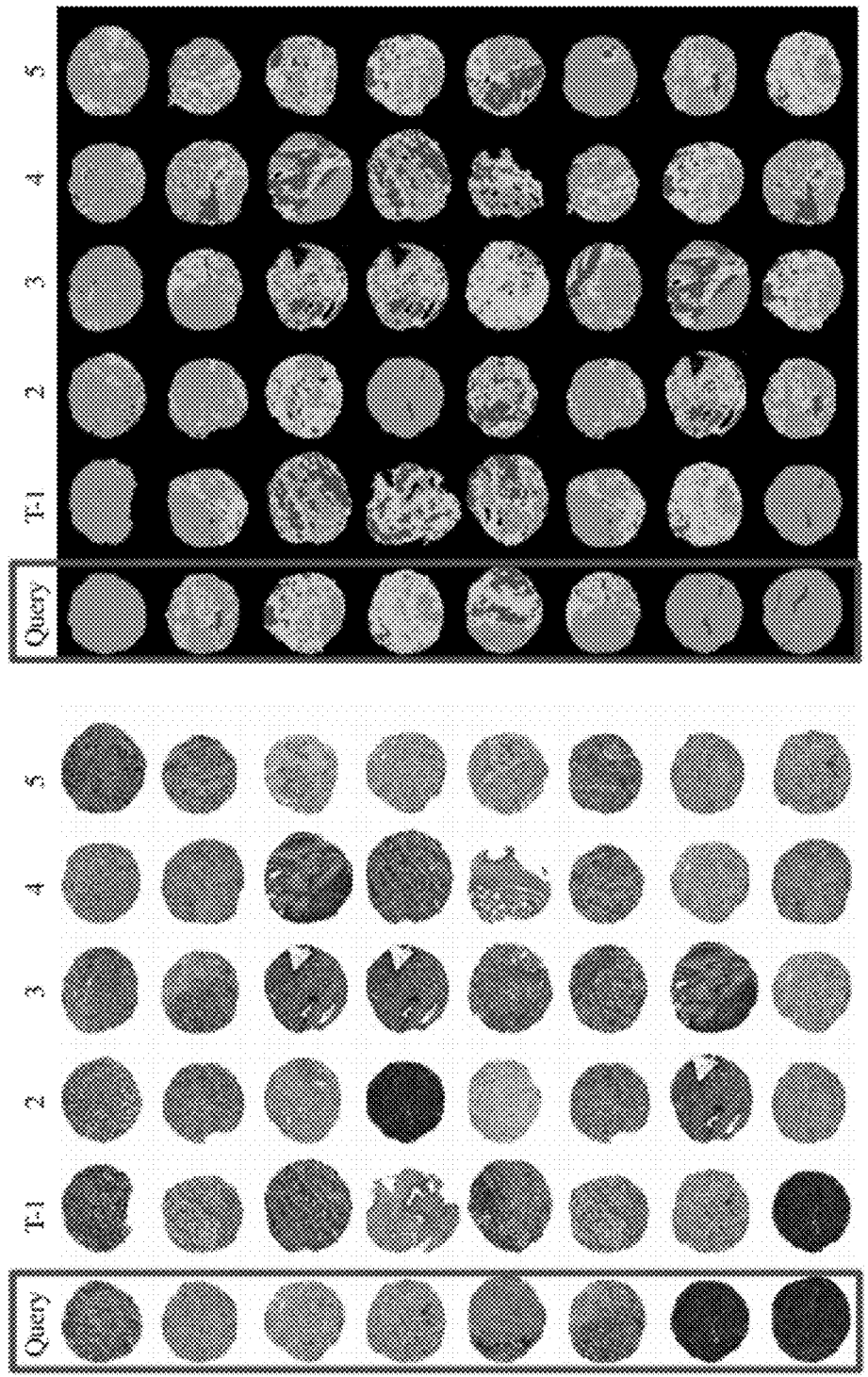
Figure 11:
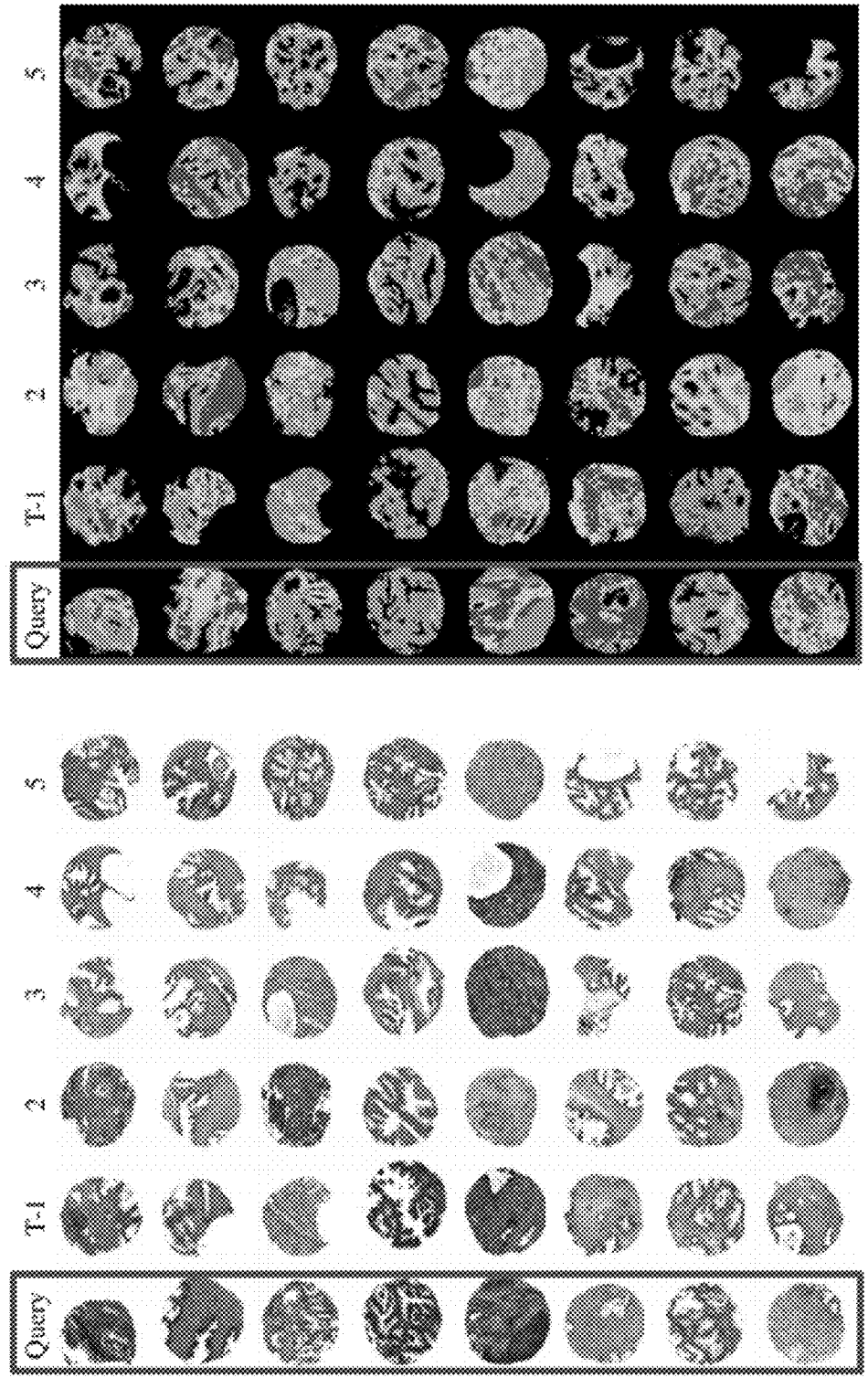
Figure 12:
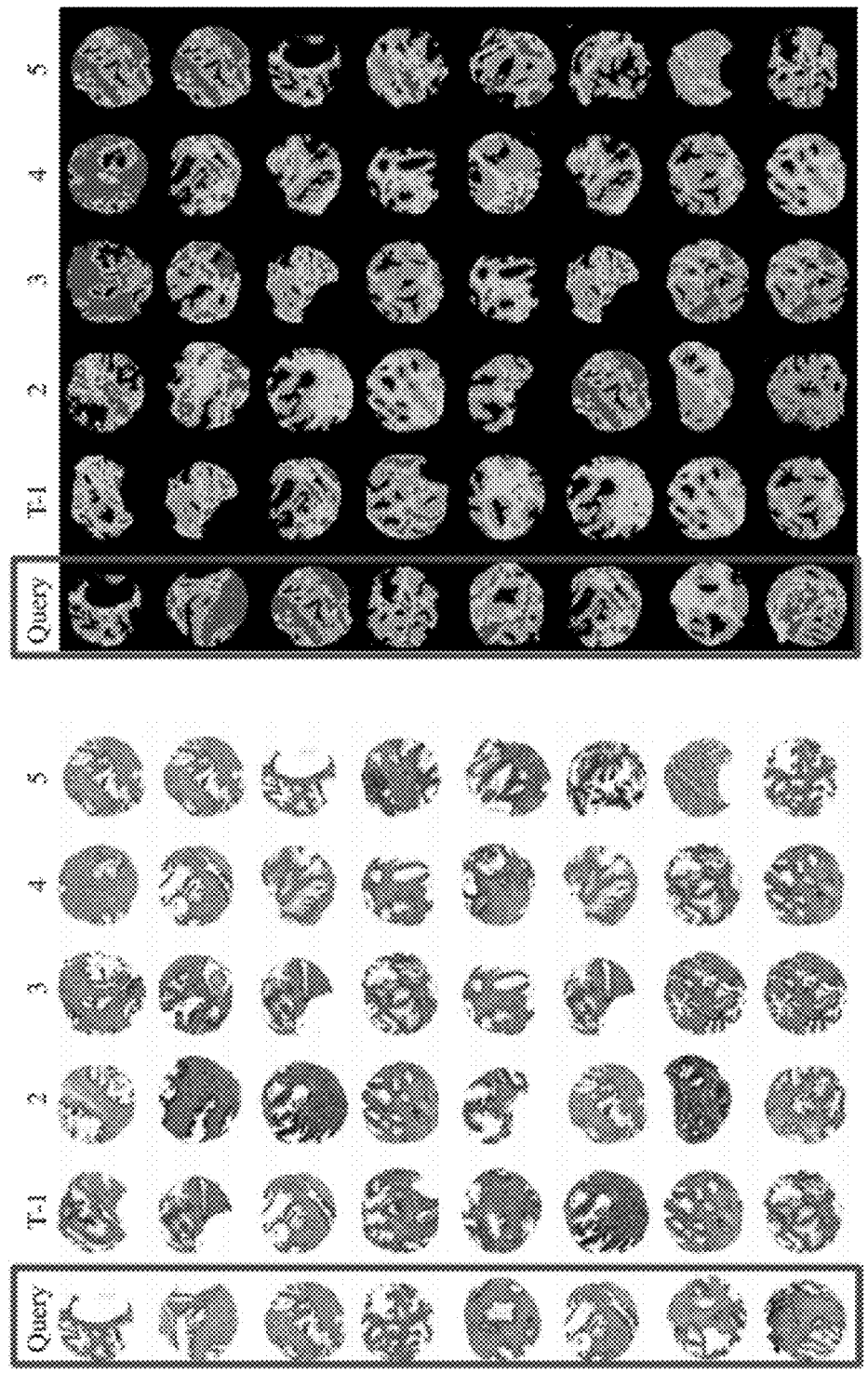

Provided herein is an automated and objective method which facilitates comprehensive information management and decision-making. The method includes the use of a database containing images of pre-examined prostate tissue samples, clinical information, and structural measurements (morphological features) of the tissues, whereby the retrieval process utilizes the structural measurements of the tissues and provides tissue samples from the database that are most similar to the test sample (FIG. 7). Although the system does not provide a diagnosis, it does provide the closest matching cases that enable a pathologist to make a diagnosis. The method uses a tissue matching process which retrieves the closest matching cases in the database with the tissue of interest. The matching process seeks to determine the true similarity between tissues in the database and a tissue of interest, and the similarity is determined by criteria to evaluate morphological properties of a tissue. The tissue similarity between the test and database samples is based on several structural properties of tissue, not solely on Gleason grade. Combining different structural components of tissue ensures better characterization of tissue structure, and thus more accurate measurement of tissue similarity can made.

The prostate tissue samples in the database can be represented or described by its morphology. Given an unknown test prostate tissue sample, the most similar tissue samples are retrieved by the retrieval process which utilizes the morphological properties of tissue. For example, the method resulted in retrieval of at least 4 and 3 good matching cases, out of 5, for ~80% and ~60% of the queries when a good match was defined as the tissue similarity score ≥5 and ≥6, respectively. Providing the closest matching cases and their clinical information from the database to pathologists will help with consistent and reliable diagnoses. Thus, the disclosed system will facilitate quality maintenance and quality improvement of cancer pathology.

Methods of identifying one or more prostate tissue samples (such as images of such samples) in a database that are closest to a test prostate sample are provided. The test prostate tissue sample and the prostate tissue samples in the database can be human or mammalian veterinary prostate samples. Prostate tissue samples in a database that are found to be the most similar based on morphological features to a test prostate sample can be identified and retrieved using the disclosed methods. The morphological features can be based on, for example, lumens and epithelial nuclei, nuclear-lumen polarization of epithelial cells as well as cellular features such as basement membrane. Exemplary morphological feature categories include, but are not limited to those related to the epithelial cells and their nuclei (such as 1) size of epithelial cells 2) size of a nucleus 3) number of nuclei 4) distance to lumen 5) distance to epithelial cell boundary 6) number of isolated nuclei 7) fraction of distant nuclei and 8) entropy of nuclei spatial distribution); those related to the lumen (such as 1) size of a lumen 2) number of lumens 3) lumen roundness 4) lumen distortion 5) lumen minimum bounding circle ratio 6) lumen convex hull ratio 7) symmetric index of lumen boundary 8) symmetric index of lumen area and 9) spatial association of lumens and cytoplasm-rich regions); as well as other quantities describing characteristics of epithelium, stroma, lumens, and glands (such as 1) number of stroma cells 2) minimum lumen distance 3) minimum gland distance 4) ratio of lumen to epithelial cells 5) ratio of epithelial cells to stroma cells 6) ratio of cell separation 7) ratio of sheets of cells 8) degree of cell dispersion and 9) spatial autocorrelation of cells). For each of these 26 feature categories, multiple feature values can be obtained, such as global (e.g., the entire sample) and local (e.g., smaller regions of the entire sample) values of the average, sum total, standard deviation, maximum, and minimum of each feature in an entire sample or in a smaller window. Thus, for each morphological feature, at least 10 different values can be obtained. In addition, multiple regions or windows in a tissue section can be examined (such as at least 2, at least 5 or at least 10 different windows), and the at least 10 different values can be obtained for each window examined. Thus, for example, for the morphological feature category "size of epithelial cells", more than one value can be extracted or obtained (or be present in the database), such as the global sum total size of epithelial cells, the local maximum size of epithelial cells, and the local standard deviation for the size of epithelial cells. In addition, multiple regions or windows can be examined, and a value for each of these three features determined for each window examined.

The method includes extracting one or more morphological features from the test prostate tissue sample. For example, one or more morphological features from the test prostate tissue sample can be extracted or determined by analyzing the sample, for example by analyzing H&E stained images and/or FT-IR images of the sample and determining values for each morphological feature. Particular exemplary methods are provided herein. In some examples, at least 5, at least 10, at least 15, at least 25, or all 26 morphological features listed above are extracted or determined for the test sample. In a specific example, at least 5, at least 10, at least 20, at least 30, at least 40, at least 50, at least 60, at least 67, at least 100, at least 200, at least 250, at least 300 or 308 morphological features listed in Table 1 or 4 are extracted from the test sample.

The morphological feature similarities between the test prostate sample and the prostate tissue samples in a database are determined. Although the database may contain information for numerous morphological features for each sample in the database, not all of the features need to be compared to the morphological features extracted from the test sample. Instead, a subset of the morphological features in the database can be used. For example, the method can include examining all available morphological features in the database, and selecting a subset to use in conjunction with the test sample. In one example, the method includes a two-stage feature selection method. In the first step, a subset of morphological features are generated, for example using the minimum-redundancy-maximal-relevance (mRMR) criterion. In the second step, the morphological feature selection continues with the morphological feature set having the best performance in the first stage as the starting point, followed by adding new features and conditional deletion(s) of already selected features, for example using the sequential floating forward selection (SFFS) method.

In one example, the selected features include lumen roundness ($G_{AVG}$), entropy of nuclei spatial distribution ($G_{TOT}$), size of lumen ($L_{MAX,AVG}$), size of nucleus ($L_{MAX,AVG}$), and size of lumen ($G_{AVG}$). In another example, the selected features include spatial association of lumen and cytoplasm ($G_{TOT}$), lumen boundary symmetry ($G_{STD}$), distance to epithelial cell boundary ($L_{MAX,AVG}$), lumen area symmetry ($G_{STD}$), and size of lumen ($L_{MAX,AVG}$).

The similarities (based on the morphological features) between the test prostate sample and the prostate tissue samples in a database can be determined. Methods of determining similarities or closeness between the database samples and the test sample are known in the art, such as Euclidean distance, Manhattan distance, Mahalanobis distance and cosine similarity. For example, similarity can be described by TMS score; the higher TMS score, the more similar.

Once the prostate tissue samples in the database that are closest or most similar to the test sample are identified (such as those k database samples that are most similar to the test prostate tissue sample), they can be retrieved from the database, for example H&E or other images of the sample can be retrieved. For example at least 1, at least 2, at least 3, at least 4, at least 5, at least 6, at least 7, at least 8, at least 9, or at least 10 different prostate tissue samples in the database can be retrieved, for example, 1 to 50, 1 to 20, 1 to 10, 3 to 20 or 3 to 10 prostate tissue samples in the database can be retrieved, such as 1, 2, 3, 4, 5, 6, 7, 8, 9 or 10 prostate tissue samples in the database can be retrieved. In some examples, the retrieved prostate tissue samples are displayed, for example by displaying images of the prostate tissue samples onto a screen or a print out. Exemplary images include H&E or other stained images, and IR-images, such as FT-IR images. For example prostate images in the database, such as images of normal prostate tissue, BPH samples, or prostate cancer tissue (such as Gleason grade 2, 3, 4 or 5), that are most similar morphologically to the test prostate tissue sample, can be retrieved from the database using a computer, and the retrieved images displayed to a user, such as a pathologist.

In some examples, the method also includes comparing the retrieved prostate tissue samples from the database to the test prostate tissue sample.

The disclosed methods can be performed on a suitably programmed computer. For example one or more, such as all, of the disclosed steps can be performed on a suitably programmed computer.

In some examples, the method has at least 80%, at least 85%, at least 90%, at least 95%, or at least 98% sensitivity. In some examples, the method has at least 80%, at least 85%, at least 90%, at least 95%, or at least 98% specificity.

In some examples, the test prostate sample is suspected of being cancerous or to be from a patient having BPH. Thus, in some examples, the method of can include selecting a subject suspected of having prostate cancer or BPH, obtaining the test prostate tissue sample from the subject, fixing the sample, H&E staining the sample, obtaining an FT-IR image of the sample, or combinations thereof. In some examples the test prostate sample has been previously fixed, stained or combinations thereof, such as H&E stained or analyzed with infrared (IR) imaging (such as FT-IR). In some examples, the method also includes obtaining IR data or immunohistochemical data from the test prostate tissue sample and/or the prostate tissue samples in the database.

As discussed in more detail below, the database can include a plurality of prostate samples, such as digital images of such samples, for example Gleason grade 2, 3, 4, and 5 cancer samples, benign prostate hyperplasia (BPH) samples, normal prostate samples, or combinations thereof. In some examples the samples in the database were previously fixed, stained, or combinations thereof, such as H&E stained or IR classified. In addition to containing the samples (or images of the samples), the database can include data for a plurality of morphological features for each sample, such as the morphological features listed in Table 1, as well as other clinical information (such as information on the age of the patient, diagnosis (e.g., Gleason grade or cancer stage), surgery type, etc.).

In some examples, the method includes generating the database. For example, the method can include obtaining prostate samples (such as normal, cancerous and BPH samples), obtaining images of H&E stained samples, obtaining FT-IR images of the samples, extracting morphological features from the samples, or combinations thereof, and inputting that information into the database.

Figure 1:
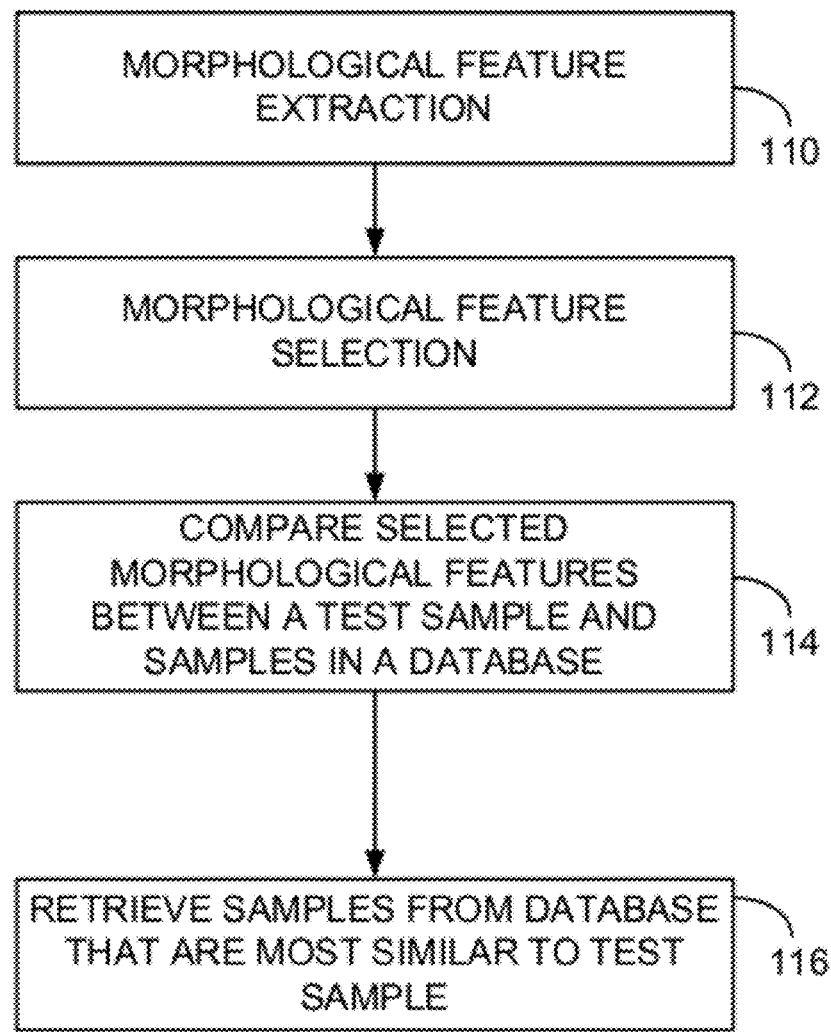
FIGS. 1-3 are flowcharts showing an exemplary method for identifying and retrieving prostate samples (or images thereof) from a database that most closely resemble a test prostate sample.
Figure 2:
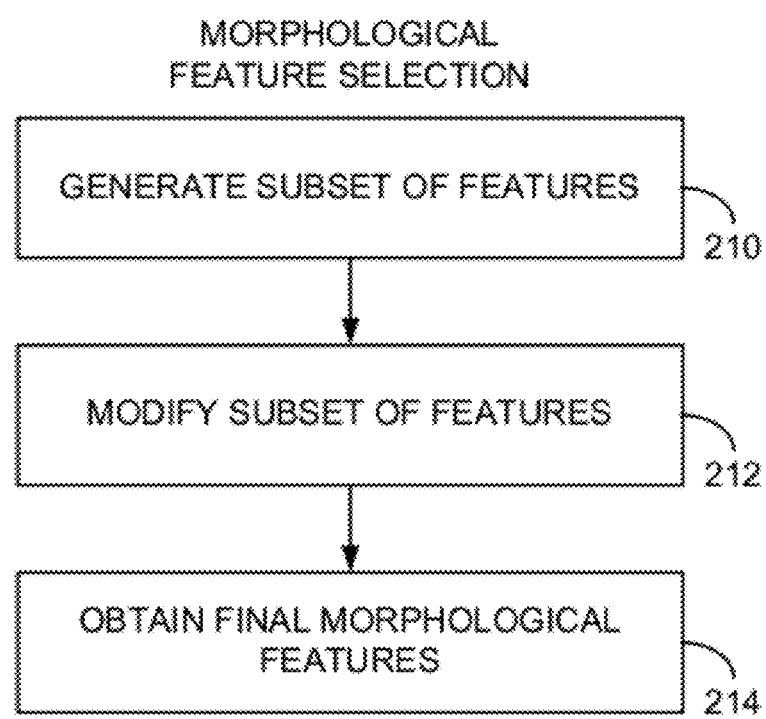
Figure 3:
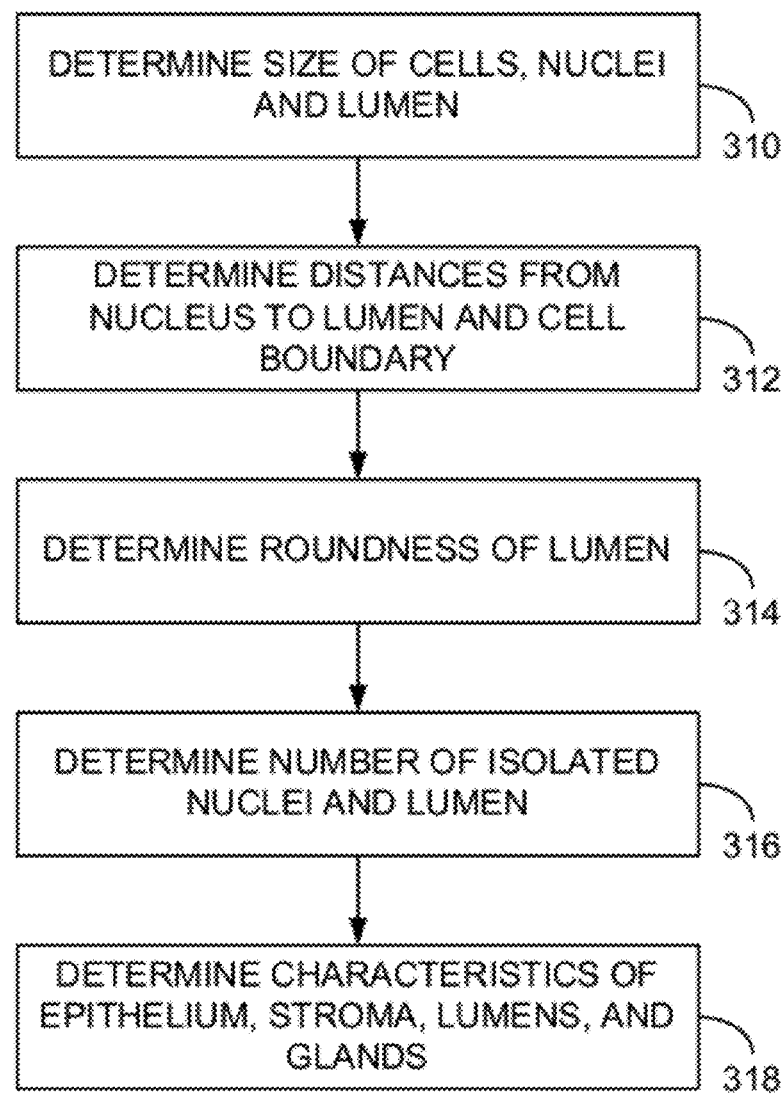

FIGS. 1-3 illustrate a method for identifying and retrieving prostate samples (or images thereof) from a database that most closely resemble a test prostate sample. Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the figures may not show the various ways in which the disclosed methods can be used in conjunction with other methods.

Any of the disclosed methods (or steps thereof) can be implemented as computer-executable instructions stored on one or more computer-readable media (e.g., non-transitory computer-readable media, such as one or more optical media discs, volatile memory components (such as DRAM or SRAM), or nonvolatile memory components (such as hard drives)) and executed on a computer (e.g., any commercially available computer, including smart phones or other mobile devices that include computing hardware). Any of the computer-executable instructions for implementing the disclosed techniques as well as any data created and used during implementation of the disclosed embodiments can be stored on one or more computer-readable media (e.g., non-transitory computer-readable media). The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, JavaScript, Adobe Flash, or any other suitable programming language. Likewise, the disclosed technology is not limited to any particular computer or type of hardware. Certain details of suitable computers and hardware are well known and need not be set forth in detail in this disclosure.

The disclosed methods, apparatus, and systems should not be construed as limiting in any way. Instead, the present disclosure is directed toward all novel and nonobvious features and aspects of the various disclosed embodiments, alone and in various combinations and subcombinations with one another. The disclosed methods, apparatus, and systems are not limited to any specific aspect or feature or combination thereof, nor do the disclosed embodiments require that any one or more specific advantages be present or problems be solved.

Turning to FIG. 1, in process block 110, morphological features are extracted from the test prostate tissue sample. In some examples, the morphological features have been previously extracted for the samples in the database, and such information is stored in the database. However, if necessary, morphological features can also be extracted from one or more reference samples (such as samples previously confirmed to be normal, BPH, or prostate cancer, such as a particular Gleason grade). For example, an image of the prostate tissue sample can be acquired and morphological features extracted (such as the 67 features listed in Table 1 or the 308 features listed in Table 4). Exemplary morphological features include those that describe size, number, shape, and distribution of the nuclei and lumens (Table 1), as well as characteristics of epithelium, stroma, lumens, and glands. Specific examples include but are not limited to, size of epithelial cells, size of a nucleus, number of nuclei, distance to lumen, distance to epithelial cell boundary, number of isolated nuclei, fraction of distant nuclei, entropy of nuclei spatial distribution, size of a lumen, number of lumens, lumen roundness, lumen distortion, lumen minimum bounding circle ratio, lumen convex hull ratio, symmetric index of lumen boundary, symmetric index of lumen area, spatial association of lumens and cytoplasm-rich regions, number of stroma cells, minimum lumen distance, minimum gland distance, ratio of lumen to epithelial cells, ratio of epithelial cells to stroma cells, ratio of cell separation, ratio of sheets of cells, degree of cell dispersion and spatial autocorrelation of cells.

Morphological features can be extracted or obtained as follows, and further details are provided in the Examples section below. Using the segmented nuclei and lumens in the image of the sample, average (AVG), standard deviation (STD), or sum total (TOT) of the feature categories are computed from the entire sample (global feature). Local features can be computed by sliding one or more windows of a fixed size (e.g., 20×20 pixels, 60×60 pixels, 100×100 pixels, 140× 140 pixels, or 180×180 pixels) throughout the sample, and AVG or TOT of the feature categories computed for each window. These quantities are summarized by computing STD, MIN, or MAX of the AVG or TOT values (local feature). A detailed description of the morphological features extraction is available in [23]. In some examples, the image of the prostate tissue sample from which morphological features are extracted is a stained image, such as an H&E stained image, or an IR image (for example obtained using FT-IR).

In process block 112, the classifier examines the morphological features of the samples in the database, and a subset of the morphological features are selected to be used on the test samples.

In process block 114, the morphological features selected in process block 112 are compared between the test prostate sample (morphological features extracted in process block 110) and the prostate samples in the database (morphological features can be retrieved from in the database). For example, similarities between the selected morphological features of the test prostate tissue sample and the prostate tissue samples in the database are computed, for example, using Euclidean distance based on the morphological features. The most similar k tissue samples to the test prostate sample are retrieved from the database (e.g., those having the same Gleason grade or having a TMS score greater than or equal to a certain score).

In process block 116, samples in the database that are most similar to the test sample are retrieved from the database. For example, the retrieved images of the samples in the database can be displayed to a user, for example by displaying on a computer screen or printout. The user can then compare the retrieved samples to the test sample, for example to make a diagnosis.

FIG. 2 is a flowchart of a method showing an exemplary morphological feature selection of process block 112. In process block 210, a subset of candidate features are generated, for example by using the minimum-redundancy-maximal-relevance (mRMR) criterion (e.g., see Peng et al., Feature selection based on mutual information: Criteria of max-dependency, max-relevance, and min-redundancy. *IEEE Transactions on Pattern Analysis and Machine Intelligence* 2005, 27(8):1226-38). Other methods such as sequentially selecting the minimum number of features (sequential forward selection) may be used. In one example, the subset of candidate features are generated by ordering features by mRMR criterion. This maximizes relevance between features and the true class label (such as normal, BPH, or prostate cancer) and minimizes redundancy between features. The performance is computed (AUC*) as increasing the number of features (e.g., up to 30). The subset of candidate features is selected by choosing the candidate feature set resulting in the best performance. In process block 212, the morphological feature selection continues by further modifying the features selected in process block 210. For example, a mRMR candidate set can be used as the starting point, which is further refined using the sequential floating forward selection (SFFS) method. In the forward step, a new morphological feature is added which increases performance the most. A conditional backward step removes one or more morphological features as long as such removal improves performance. In process block 214, the final set of morphological features is obtained, which will be used to compare the test sample to the samples in the database.

FIG. 3 is a flowchart of a method for extracting morphological features from nuclei and lumen. There are a variety of extraction methods that can be used. FIG. 3 shows some examples of features that can be extracted. In process block 310, the size of cells, nuclei and lumen can be determined. In process block 312, distances from the nucleus to the lumen and cell boundaries can be determined. In process block 314, the roundness of the lumen can be determined. In process block 316, the number of isolated nuclei and lumen can be determined. In process block 318, the characteristics of epithelium, stroma, lumens, and glands can be determined. In one example, the feature categories can generally be described in five groups—size, number, distance, shape and distribution. The following list is an exemplary list of features.

1) size of epithelial cells, nuclei, and lumen
2) number of nuclei (total, isolated, and far) and lumens
3) distance from nucleus to lumen and cell boundary
4) lumen shape: distortion, roundness, minimum bounding circle ratio, convex ratio, symmetric index of lumen boundary and area
5) spatial distribution: entropy of spatial distribution of nuclei and spatial association of lumen and cytoplasm The list of morphological features can further include characteristics of epithelium, stroma, lumens, and glands, such as spatial association of lumens and cytoplasm-rich regions, number of stroma cells, minimum lumen distance, minimum gland distance, ratio of lumen to epithelial cells, ratio of epithelial cells to stroma cells, ratio of cell separation, ratio of sheets of cells, degree of cell dispersion and spatial autocorrelation of cells.

FIG. 4 shows an exemplary method for extracting morphological features from a prostate tissue sample from which an H&E image and an IR image have been obtained.

Biological Samples

The test prostate samples, as well as the prostate samples in the database, can be obtained from any prostate tissue, such as a human subject suspected of having prostate cancer or BPH, as well as normal prostate tissue. A typical subject is a human male; however, any mammal that has a prostate that may develop cancer can serve as a source of a sample useful in the disclosed methods. Exemplary biological samples useful in a disclosed method include tissue samples (such as, prostate biopsies and/or prostatectomy tissues) or prostate cell samples (such as can be collected by prostate massage, in the urine, in semen, in fine needle aspirates, as well as circulating tumor cells (CTCs) in the blood).

Samples may be fresh or processed post-collection (e.g., for archiving purposes). In some examples, processed samples may be fixed (e.g., formalin-fixed) and/or wax- (e.g., paraffin-) embedded. Fixatives for mounted cell and tissue preparations are well known in the art and include, without limitation, 95% alcoholic Bouin's fixative; 95% alcohol fixative; B5 fixative, Bouin's fixative, formalin fixative, Karnovsky's fixative (glutaraldehyde), Hartman's fixative, Hollande's fixative, Orth's solution (dichromate fixative), and Zenker's fixative (see, e.g., Carson, *Histotechology: A Self-Instructional Text*, Chicago:ASCP Press, 1997).

In some examples, the sample (or a fraction thereof) is present on a solid support. Solid supports useful in a disclosed method need only bear the biological sample and can permit the convenient detection of components (e.g., lumens, nuclei, epithelial cells) in the sample. Exemplary supports include microscope slides (e.g., glass microscope slides or plastic microscope slides), coverslips (e.g., glass coverslips or plastic coverslips), tissue culture dishes, multi-well plates, membranes (e.g., nitrocellulose or polyvinylidene fluoride (PVDF)) or BIACORE™ chips.

In some examples, the disclosed methods can include obtaining the test sample from the patient. In some examples, the disclosed methods can include staining and/or imaging of the test sample, such as staining the sample with H&E and imaging the sample, analyzing the test sample using FT-IR, or combinations thereof.

Databases

The disclosure also provides databases, for example that can be used with the disclosed methods. The database includes pre-examined prostate tissues (e.g., images of such tissues) and morphological information for each sample. When performing the disclosed methods, a pathologist may indicate that certain matches were better than others, resulting in an updating of the database and matching algorithms as needed, which may be conducted in real-time.

In some examples, the database includes a plurality of prostate tissue samples, such as prostate cancer tissue samples, normal prostate tissue samples, BPH tissue samples, or combinations thereof. For example, the database can include at least 100 different samples, such as at least 150, at least 200, at least 500, or even at least 1000 different samples. Exemplary prostate cancer tissue samples include those with a Gleason grade of 2, 3, 4, or 5, normal prostate tissue samples (that is those that are cancer, tumor, or BPH free), and BPH tissue samples. In some examples, the data base includes at least 20 each of Gleason grade of 2, 3, 4, and 5, normal prostate tissue samples, and BPH tissue samples, such as at least 30, at least 40, at least 50, at least 100, at least 500, or at least 1000 of each sample type.

In some examples, the database includes a plurality of prostate cancer tissue samples, such as at least at least 100 different prostate cancer tissue samples, at least 150, at least 200, at least 500, at least 1000, or at least 5000 different prostate cancer tissue samples. In some examples, such a database of prostate cancer tissue samples includes a plurality of samples having a Gleason grade of 2, 3, 4, and 5.

The database can include digital images of prostate tissue samples, structural properties for each sample (e.g., one or more of the nine parameters listed in Table 3), morphological features for each sample (e.g., those listed in Table 1 or Table 4), clinical and pathological information for sample (e.g., normal or cancerous, Gleason grade, age, surgery type, etc.), as well as the samples themselves. In some examples the tissues are fixed and may be embedded. The tissues may or may not be stained, for example with H&E or other histological dye that permits morphological feature extraction. The tissues may or may not be labeled, for example with an antibody or probe, such as a marker specific for prostate cancer. In some examples, the database includes IR chemical imaging data for one or more samples in the database. In some examples, the database includes digital images of H&E stained samples for one or more samples in the database. In some examples, the database includes digital images of H&E stained tissues, FT-IR imaging data, morphologic criteria to determine tissue similarity (e.g., see Table 3), and morphological features (e.g., those listed in Table 1 and Table 4) for each sample in the database.

Computer Readable Medium

The disclosure also provides a computer-readable storage medium having instructions thereon for performing a method of identifying one or more prostate tissue samples in a database that are closest to a test prostate sample. Such a computer-readable storage medium, can include instructions for extracting a plurality of morphological features from a test prostate tissue sample; retrieving a plurality of morphological features from a plurality of prostate tissue samples in a database; comparing the plurality of morphological features from a test prostate tissue sample to the same plurality of morphological features from the plurality of prostate tissue samples in the database; determining similarities based on the plurality of morphological features between the test prostate sample and a plurality of prostate tissue samples in the database; and retrieving from the database one or more prostate tissue samples in the database that are the most similar to the test prostate tissue sample based on the plurality of morphological features. In some examples, the computer-readable storage medium further includes instructions for outputting the one or more prostate tissue samples in the database that were retrieved. In some examples, the computer-readable storage medium further includes instructions for selecting a subset of the morphological features from the samples in the databases, wherein the subset of morphological features are compared between the samples in the database to the test sample.

The plurality of morphological features from the test prostate tissue sample can be extracted by objective numerical algorithms implemented in computer software (for brevity "algorithms"). The morphological features from the prostate tissue samples in a database can be retrieved by algorithms. The plurality of morphological features from the test prostate tissue sample can be compared to the same plurality of morphological features from the plurality of prostate tissue samples in the database by algorithms. In some examples, a subset of the morphological features are compared. Similarities based on the plurality of morphological features between the test prostate sample and a plurality of prostate tissue samples in the database can be determined by algorithms. One or more prostate tissue samples in the database that are the most similar to the test prostate tissue sample based on the plurality of morphological features can be retrieved by algorithms, and can be outputted.

The computer-readable storage medium can further include information for comparing the retrieved prostate tissue samples from the database to the test prostate tissue sample.

It is shown herein that morphological features are able to characterize prostate tissues. Here, 67 morphological features based on lumens and epithelial nuclei, or 308 morphological features based on lumens and epithelial nuclei as well as characteristics of epithelium, stroma, lumens, and glands, were extracted from each tissue sample. Each database contained the morphological features for the tissue samples which had been previously examined and classified (e.g., noted to be normal or cancerous) by pathologists.

The morphological features from a test (query) prostate tissue sample whose prostate cancer status was unknown were extracted. The similarities between the test sample and the tissue samples in the database were then computed using Euclidean distance or Ranking-SVM based on the morphological features. Lastly, the most similar k (a user-determined integer) tissue samples to the query are were received from the database.

In one example, the method was performed using a dataset composed of 181 tissue samples. In the dataset, 5, 23, 66, and 21 tissue samples are Gleason grade 2, 3, 4, and 5 cancer ("Cancer"), respectively, and 20 and 46 tissue samples are BPH and normal ("Benign"), respectively. Due to the small number of tissue samples, Gleason grade 2 was ignored for the further consideration. Each tissue sample was represented by 67 morphological features (Table 1). To measure the performance, the k-nearest neighbor (kNN) algorithm was used and the grade of the query predicted by majority voting. Both accuracy and kappa-coefficient were computed for the predictions.

Leave-one-out cross-validation (LOOCV) was performed on the dataset. LOOCV leaves one example as a validation data and uses the remaining examples as training data, and iterates this over every example. In this method, the validation data is the query, and the training data is regarded as the database. The number of tissue samples in each grade in the dataset varied, which might affect the prediction made by kNN algorithm. To tackle the problem, the same number of tissue samples from each grade was randomly selected and LOOCV performed on the sub-dataset. This was repeated 100 times, and the average accuracy and kappa-coefficient were computed over the repeats, to provide robust and reliable assessments despite the stochastic nature of constructing the sub-dataset.

Figures 5A, 5B, 5C, 5D:
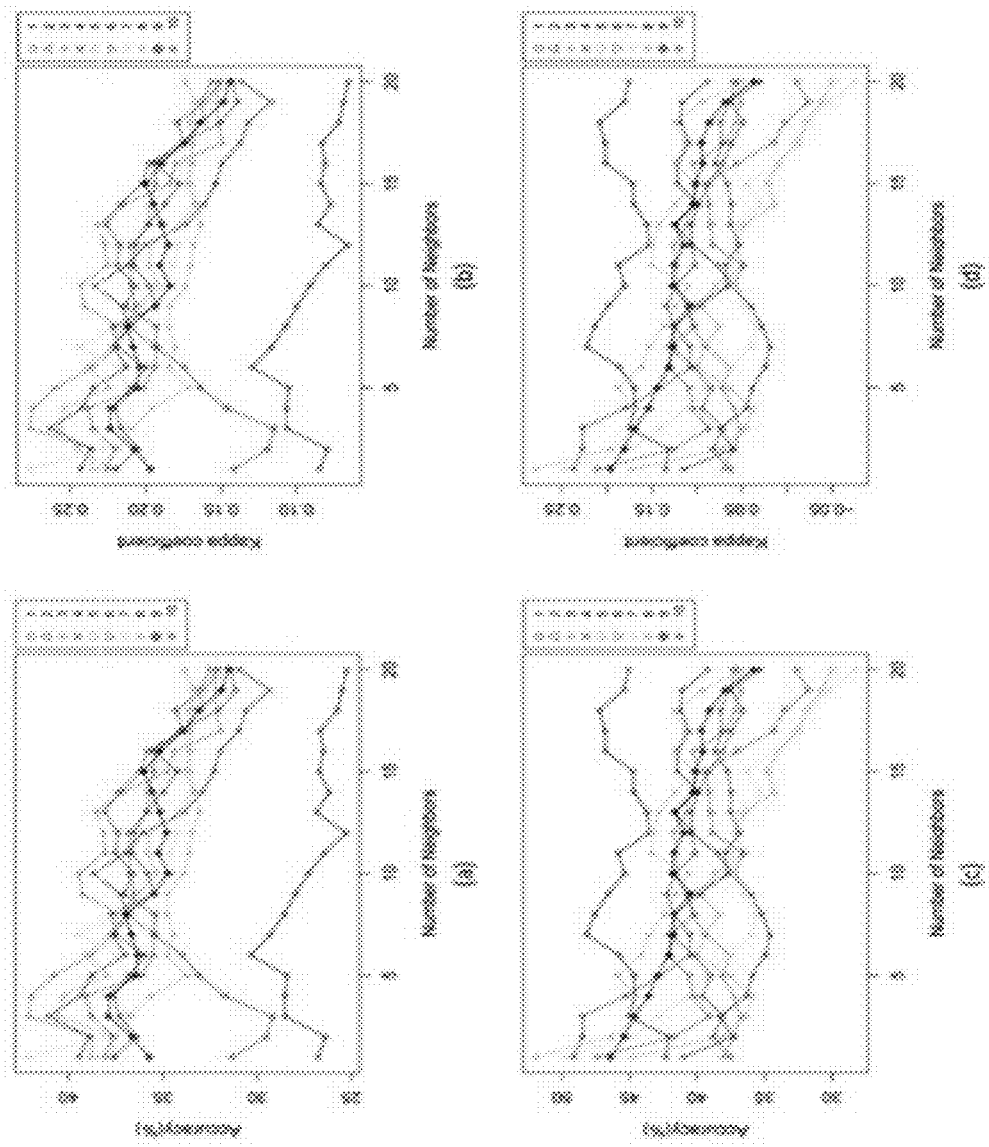
FIGS. 5A-5D are a series of graphs showing the average accuracy and kappa coefficient. (a), (b) grading for both "Cancer" and "Benign" samples. (c), (d) grading for "Cancer" samples. Each line depicts the accuracy and kappa coefficient values of the corresponding number of features.
Figure 6A:
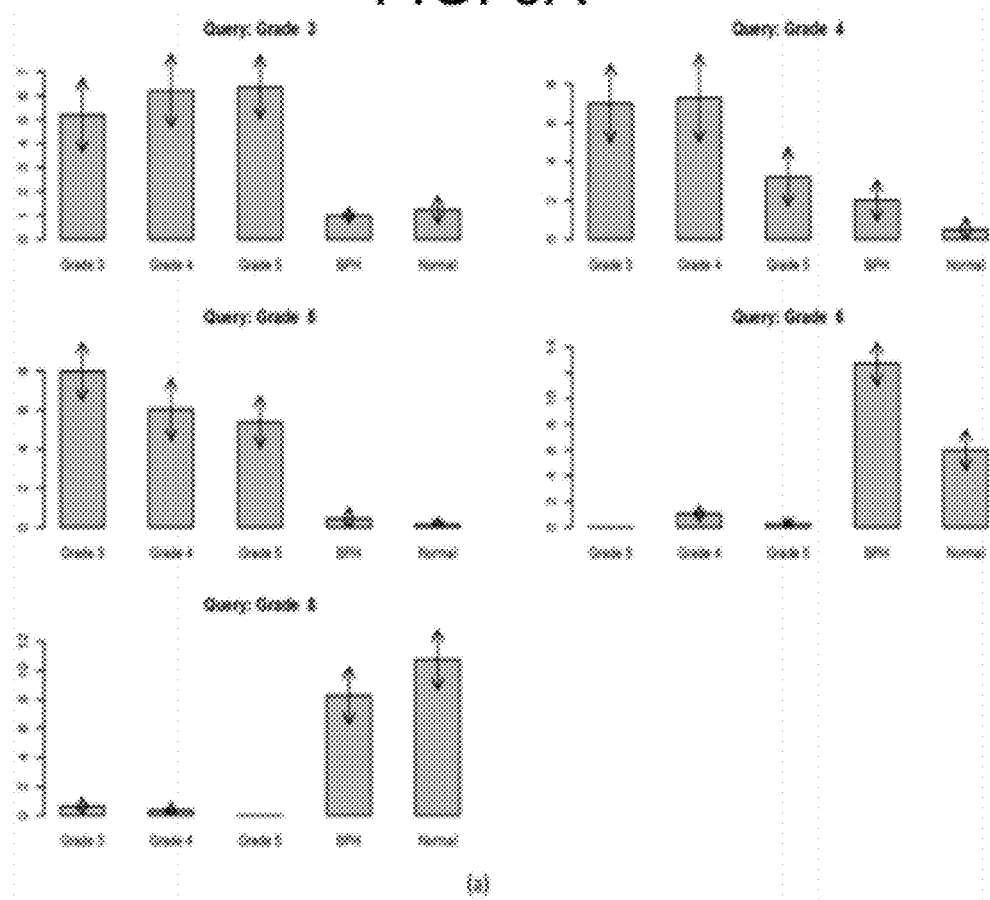
FIGS. 6A-6B are a series of bar graphs showing the distribution of the grade of the retrieved samples. (a) grading for both "Cancer" and "Benign" samples. (b) grading for "Cancer" samples. For the samples in each grade, the grade of retrieved samples are counted and the average number of samples are shown. The arrows denote ±1 standard deviation of the number of samples.
Figure 6B:
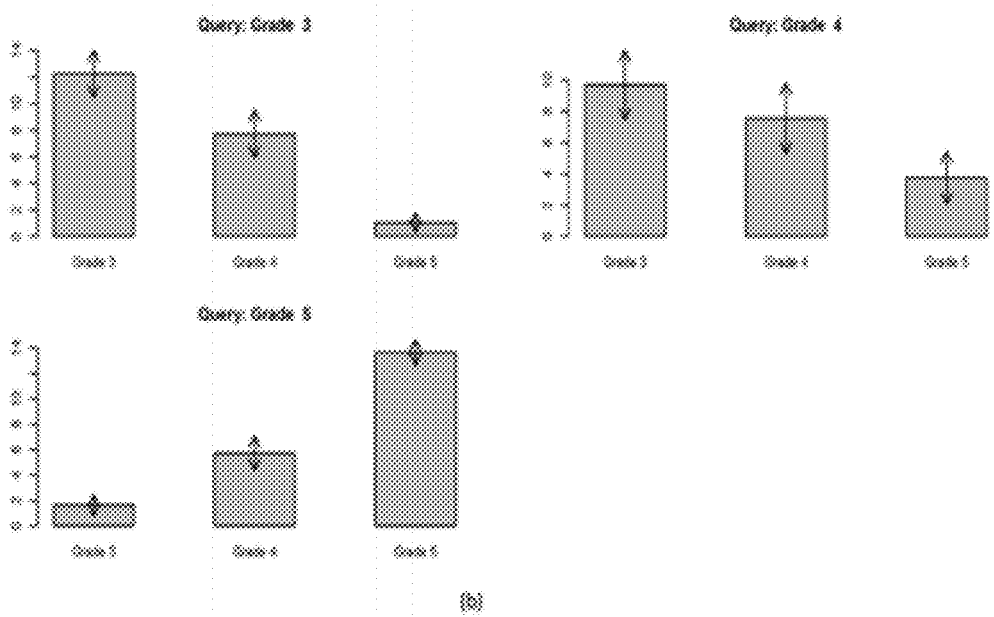

The method is subject to the choice of the number of nearest neighbors to consider for the prediction and the number of features to use for the similarity computation. To examine the effect of them, the average accuracy and kappa-coefficient was computed over 100 repeats as increasing the two factors (FIG. 5A-D). The accuracy decreases as increasing the number of nearest neighbors, and the more features we use, the higher accuracy achieved. The highest average accuracy achieved for grading both "Cancer" and "Benign" samples (i.e., 5 grades) was 42% using 7 features and 1 nearest neighbor (FIG. 5A). By using 8 features and 1 nearest neighbor, the highest accuracy of 52% achieved for grading only "Cancer" samples (i.e., 3 grades) (FIG. 5C). Both cases also achieved the average Kappa coefficient of 0.27 (FIG. 5A, 5D). In FIG. 6, the distribution of the grade of the retrieved samples is shown. Distinction between "Cancer" and "Benign" samples is obvious (FIG. 6A), but among "Cancer", the retrieved samples often do not belong to the same grade with the query, especially between Gleason grade 3 and 4.

In a second example, the method was performed using a dataset composed of 114 tissue samples. In the dataset, all of the samples were cancerous. Each tissue sample was represented by 308 morphological features, as well as nine structural criteria (Table 3) to permit for a determination of the tissue morphological similarity between the samples in the database. To retrieve the most similar samples from the database, Ranking-SVM was used. To evaluate the tissue retrieval system, K-fold cross-validation was performed FIG. 7 shows an example of a test sample that has been compared to the database, along with the retried samples, using the disclosed methods.

Example 1

This example describes methods used to identify in a database of about 180 prostate samples, those samples that are most similar to test prostate cancer samples.

Feature Extraction

Morphological features were used characterize prostate tissues. Here, 67 morphological features, which are based on lumens and epithelial nuclei, were extracted from each tissue sample (see Table 1). Thus, these 67 features were determined for the test prostate sample, and for each prostate sample in the database. For the prostate samples in the database, these 67 features can be determined once, and then the information stored and retrieved later to enable the comparison. Thus, the database includes the morphological features for numerous tissue samples which have already been examined by pathologists. FIGS. 16A-16G shows how seven exemplary features were extracted.

TABLE 1

| Feature Name | Description | Type |
| --- | --- | --- |
| Size of epithelial cells | Number of pixels in epithelial cells. | $G_{TOT}$, $L_{MAX}$, $L_{STD}$ |
| Size of nucleus | Size of a nucleus. | $G_{AVG}$, $G_{TOT}$, $G_{STD}$, $L_{STD}$, $L_{STD,TOT}$, $L_{MAX,AVG}$, $L_{MAX,TOT}$ |
| Number of nuclei | Number of Nuclei. | $G_{TOT}$, $L_{STD}$, $L_{MAX,TOT}$ |
| Distance to lumen | Distance from the center of a nucleus to the boundary of the closest lumen. | $L_{AVG}$, $L_{STD}$, $L_{MAX,AVG}$, $L_{MIN,AVG}$ |
| Distance to epithelial cell boundary | Distance from center of the nucleus to the boundary of the epithelial cell. Epithelial cells are estimated by drawing a Voronois diagram of the nuclei. | $L_{AVG}$, $L_{STD}$, $L_{MAX,AVG}$, $L_{MIN,AVG}$ |
| Number of isolated nuclei | Number of nuclei without having a neighboring nucleus within a distance (<20 um) from the center of each nucleus. | $G_{TOT}$, $L_{STD}$, $L_{MAX,TOT}$ |
| Fraction of distant nuclei | Fraction of nuclei away from lumens (>30 um). | $G_{TOT}$ |
| Entropy of nuclei spatial distribution | $H(Nuclei) = -\sum_{i=1}^{n}\sum_{j=1}^{n} p(x_{ij}) \log p(x_{ij})$ where p() denotes the probability mass function of the number of nuclei in a partition, $x_{ij}$ denotes the number of nuclei in (i, j) the partition. | $G_{TOT}$, $L_{STD}$, $L_{MAX,TOT}$ |
| Size of lumen | Number of pixels in a lumen. | $G_{AVG}$, $G_{TOT}$, $G_{STD}$, $L_{MAX,AVG}$, $L_{MAX,TOT}$, $L_{STD,AVG}$, $L_{STD,TOT}$, $L_{MAX,AVG}^*$, $L_{MAX,TOT}^*$, $L_{STD,AVG}^*$, $L_{STD,TOT}^*$ |
| Number of lumen | Number of lumens. | $G_{TOT}$, $L_{MAX}$, $L_{STD}$ |
| Lumen roundness | $\frac{L_{peri}}{2L_{area}}r$ where $L_{peri}$ and $L_{area}$ are the perimeter and the size of a lumen, respectively, and r is the radius of a circle with the size of $L_{area}$. | $G_{AVG}$, $G_{STD}$, $L_{MAX,AVG}$, $L_{STD,AVG}$ |
| Lumen distortion | $\frac{STD(d_{Lcb})}{AVG(d_{Lcb})}$ where $d_{Lcb}$ is the distance from the center of a lumen to the boundary of a lumen. | $G_{AVG}$, $G_{STD}$, $L_{MAX,AVG}$, $L_{STD,AVG}$ |
| Lumen minimum bounding circle ratio | Ratio of the size of a minimum bounding circle of a lumen to the size of the lumen. | $G_{AVG}$, $G_{STD}$, $L_{MAX,AVG}$, $L_{STD,AVG}$ |
| Lumen convex hull ratio | Ratio of the size of a convex hull of a lumen to the size of the lumen. | $G_{AVG}$, $G_{STD}$, $L_{MAX,AVG}$, $L_{STD,AVG}$ |
| Lumen boundary symmetry | $\frac{\sum |L_{Ti} - L_{Bi}|}{\sum (L_{Ti} + L_{Bi})} + \frac{\sum |L_{Ri} - L_{Li}|}{\sum (L_{Ri} + L_{Li})}$ where $L_{Ti}$ and $L_{Bi}$ are vertical distances from a vertical axis to the boundary of a lumen, $L_{Li}$ and $L_{Ri}$ are horizontal distances from a horizontal axis to the boundary of a lumen. | $G_{AVG}$, $G_{STD}$, $L_{MAX,AVG}$, $L_{STD,AVG}$ |

TABLE 1-continued

| Feature Name | Description | Type |
|---|---|---|
| Lumen area symmetry | $\frac{|L_{Larea} - L_{Rarea}|}{L_{Larea} + L_{Rarea}} + \frac{|L_{Tarea} - L_{Barea}|}{L_{Tarea} + L_{Barea}}$ wher $L_{Larea}$, $L_{Rarea}$, $L_{Tarea}$, and $L_{Barea}$ are the size of left, right, top, and bottom quadrants, respectively. | $G_{AVG}$, $G_{STD}$, $L_{MAX,AVG}$, $L_{STD,AVG}$ |
| Spatial association of lumen and cytoplasm | $\frac{\eta_{adj}}{\eta_{adj} + \eta_{dis}}$ where $\eta_{dis}$ is a set of cytoplasm-rich pixels distant to lumens and $\eta_{adj}$ is a set of cytoplasm-rich pixels adjacent to lumens. | $G_{TOT}$ |

List of features.
G and L denote global and local features, respectively.
AVG, TOT, STD, MAX and MIN represent average, sum total, standard deviation, maximum, and minimum of features in an entire sample or in a window.
*indicates that only a part of a lumen within a window is taken into account in computing feature values.

Feature Selection

Feature selection is the step where the classifier examines all available features (67 here) of the database samples (training data), and selects a subset to use on the test samples. This selection is generally based on the criterion of high accuracy on training data, but also strives to ensure generalizability beyond the training data. A two-stage feature selection approach was adopted. To determine samples into "Cancer" and "Benign" based on the example database, the 5 most frequently selected features are lumen roundness ($G_{AVG}$), entropy of nuclei spatial distribution ($G_{TOT}$), size of lumen ($L_{MAX,AVG}$*), size of nucleus ($L_{MAX,AVG}$), and size of lumen ($G_{AVG}$) in order of frequency. Spatial association of lumen and cytoplasm ($G_{TOT}$), lumen boundary symmetry ($G_{STD}$), distance to epithelial cell boundary ($L_{MAX,AVG}$), lumen area symmetry ($G_{STD}$), and size of lumen ($L_{MAX,AVG}$), in order of frequency, are the 5 most frequently selected features for grading only "Cancer" samples (i.e., 3 grades) based on the example database. Features describing lumens are important for both cases. In particular, size of lumen is significant for both cases. For "Cancer" and "Benign" classification, two nuclei features are frequent.

In the first stage, a subset of candidate features was generated by using the minimum-redundancy-maximal-relevance (mRMR) criterion. In each iteration, given a feature set chosen thus far, this method chooses the single additional feature that is least redundant with the chosen features, while being highly correlated with the class label. In the second stage, feature selection continues with the mRMR candidate set as the starting point, using the sequential floating forward selection (SFFS) method. This method sequentially adds new features followed by conditional deletion(s) of already selected features. The classification capability of a feature set, required for feature selection, is measured by the accuracy, obtained by Leave-One-Out cross-validation on the training set.

Tissue Matching

Morphological features are extracted from individual prostate tissue samples and used to construct the database of known prostate tissue samples. The search for the tissue samples in the database that are similar to a test sample is based on the morphological features. The morphological features are extracted from the test prostate tissue sample. The similarities between the test prostate tissue sample and the prostate tissue samples in the database are computed, for example, using Euclidean distance based on the morphological features. The most similar k tissue samples to the test prostate sample are retrieved from the database.

Database

To assess the validity of the method, a dataset composed of 181 tissue samples was used. In the dataset, 5, 23, 66, and 21 tissue samples are Gleason grade 2, 3, 4, and 5 cancer ("Cancer"), respectively, and 20 and 46 tissue samples are BPH and normal ("Benign"), respectively.

Classification

To measure the performance of the method, the k-nearest neighbor (kNN) algorithm was used and predicted the grade of the query by majority voting (k=5). The tissue samples were first classified into "Benign" and "Cancer", and since pathologists may be more interested in grading of cancerous tissue samples, the method was also applied only to the "Cancer" tissue samples; i.e., Gleason grade 3, 4, and 5 samples. Due to the small number of tissue samples, Gleason grade 2 was ignored for further consideration.

Classification on Each Dataset

K-fold cross-validation was performed on the datasets. The dataset was divided into K roughly equal-sized partitions, one partition was left out as the "test data", the classifier was trained on the union of the remaining K−1 partitions (the "training data") and evaluated on the test data. This was repeated K times, with different choices of the left-out partition (we set K=10). In each repetition, Leave-one-out cross-validation on the training data was used to select the feature set with the highest accuracy. The number of tissue samples in each grade in the dataset varies. The imbalance in the dataset could affect the prediction made by kNN algorithm. To address this, the same number of tissue samples from each grade was randomly sampled and cross-validation performed. The correct and incorrect predictions in the test data, across all K repetitions, were combined to compute the accuracy of the dataset. Since the sampling and the cross-validation make random choice in partitioning the dataset, the entire sampling and cross-validation pipeline was repeated 100 times.

As shown in Table 2, the average accuracy for "Benign" and "Cancer" classification was 96.53%, and the average sensitivity and specificity were 95.46% and 97.59%, respectively. For "Cancer" Gleason grading, the average accuracy of 68.33% was obtained.

TABLE 2

Classification results via sampling and cross-validation.

| Dataset | Accuracy (%) AVG | Accuracy (%) STD | Sensitivity (%) AVG | Sensitivity (%) STD | Specificity (%) AVG | Specificity (%) STD | $M_f$ |
|---|---|---|---|---|---|---|---|
| "Benign" and "Cancer" | 96.53 | 1.15 | 95.46 | 2.12 | 97.59 | 1.20 | 11 |
| "Cancer" | 68.33 | 5.83 | • | • | • | • | 8 |

AVG and STD denote average and standard deviation across 100 repeats of cross-validation. $M_f$ is the median size of the feature set obtained by feature selection from training data.

Examination of Retrieved Samples

Figure 13A:
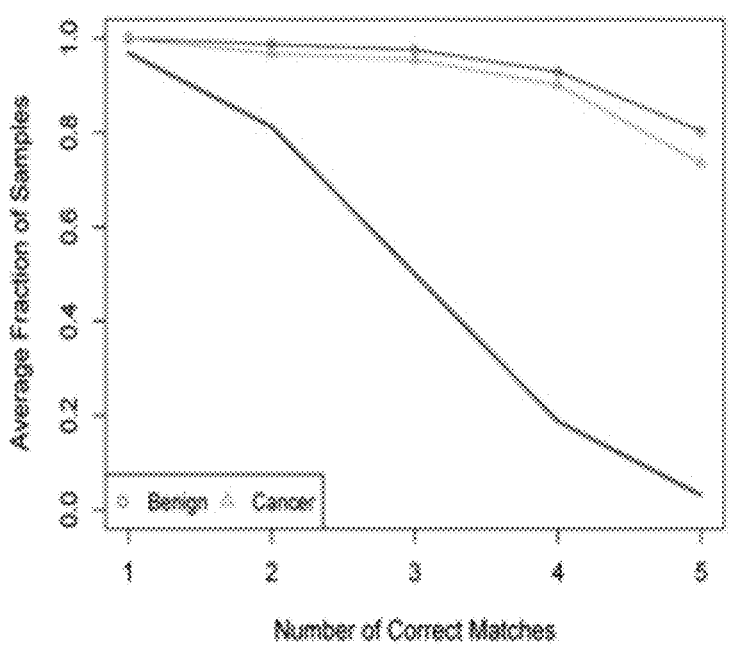
FIGS. 13A and 13B are graphs showing the fraction of queries retrieving at least i number of the same grade samples (i=1, 2, 3, 4, 5).
Figure 13B:
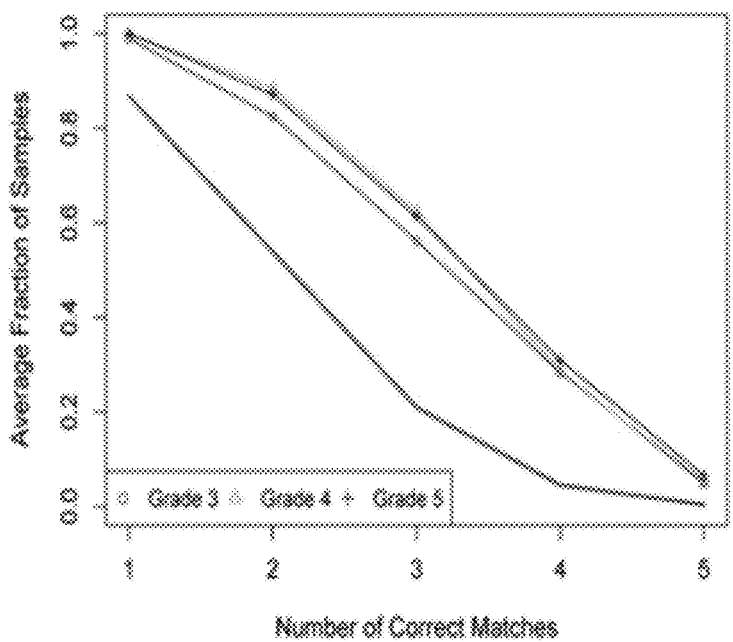

The retrieved samples from the database were compared to each query based on Gleason grade. FIGS. 8-12 show H&E stained images (on the left) and IR images (on the right) for several test samples (query) and the corresponding retrieved samples from the database (T1-5). The number of retrieved samples belonging to the same grade with the query was counted. FIGS. 13A-B show that the fraction of queries which has at least i number of retrieved samples possessing the same grade with the query (i=1, 2, 3, 4, 5). For "Benign" and "Cancer" dataset, ~80% of "Benign" queries and ~73% of "Cancer" queries retrieved the samples having the same grade with them. Although this was not the case for "Cancer" dataset, still these were obviously higher than the random chance (bottom line in FIG. 13).

Figure 14A:
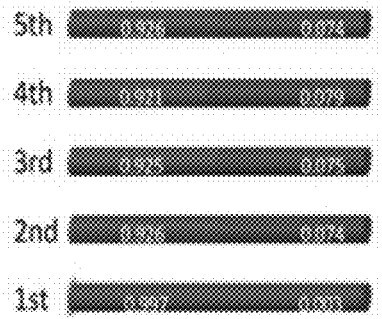
FIGS. 14A and 14B are graphs showing the portion of retrieved samples. (A) Benign. (B) Cancer.
Figure 14B:
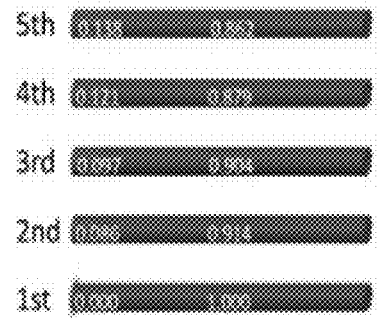
Figure 15A:
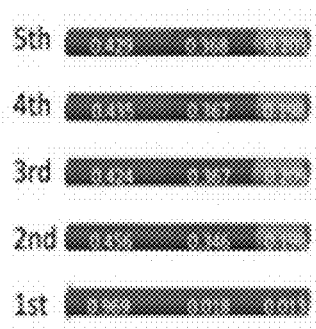
FIGS. 15A-15C are graphs showing the portion of retrieved samples. (A) Grade 3. (B) Grade 4. (C) Grade 5.
Figure 15B:
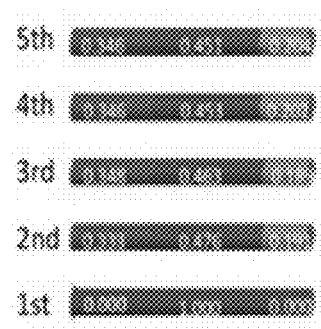
Figure 15C:
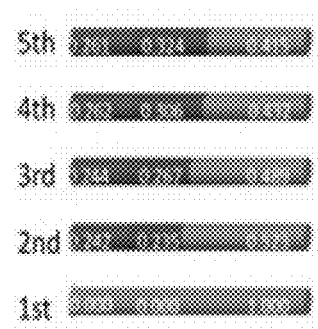
Figures 16A, 16B, 16C, 16D, 16E, 16F, 16G:
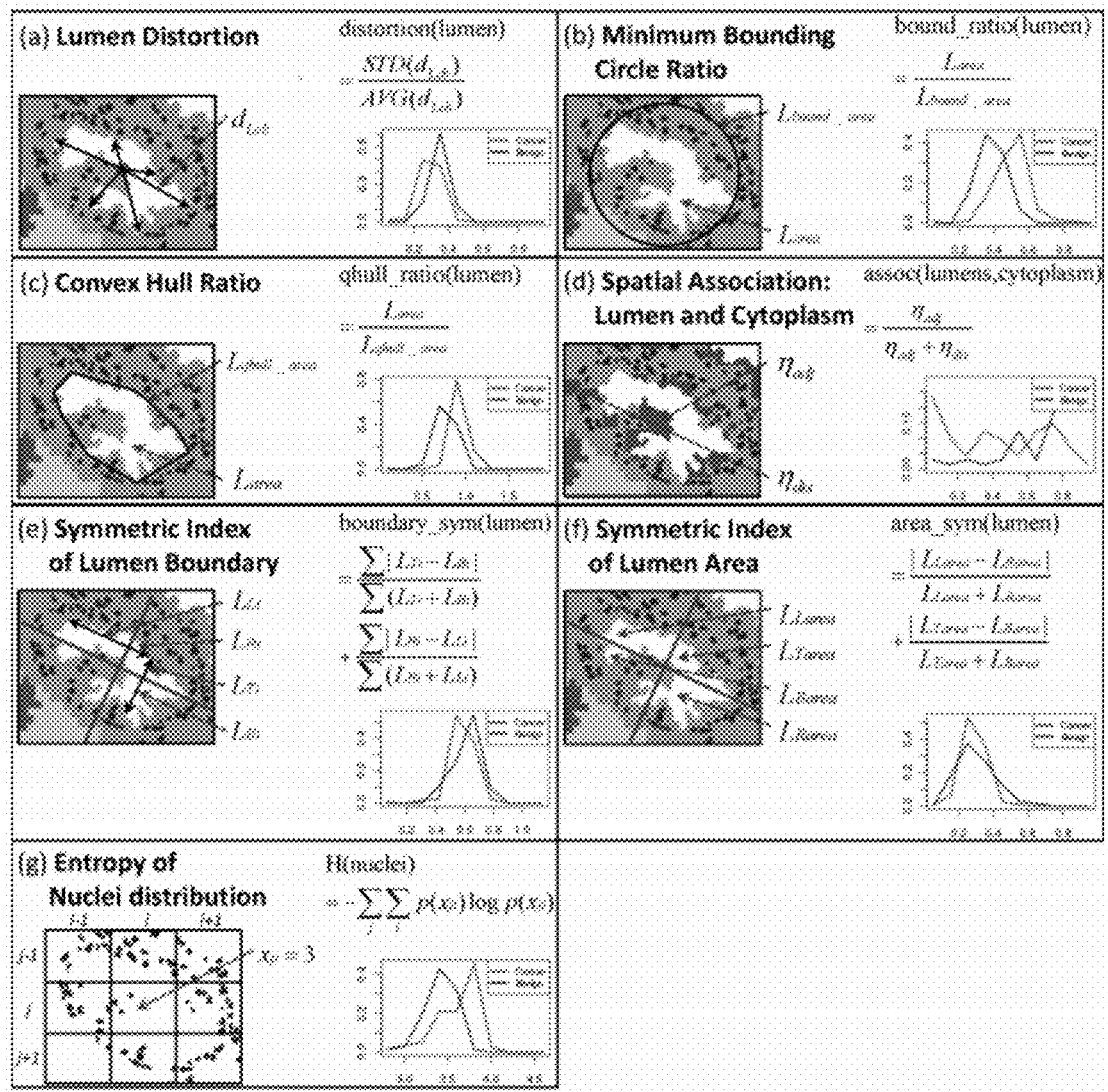
FIGS. 16A-16G show exemplary morphological features that can be extracted from the test sample and samples in a database.

In addition, the portion of each grade at ith match was measured. For "Benign" and "Cancer" dataset (FIGS. 14A and B), regardless of the ranking of the retrieved samples, the grade of them was mostly consistent with the query. For "Cancer" dataset (FIGS. 15A-C), the closest match tends to possess the same grade with the query, but the drop in the portion of the same grade samples was quite significant; it was still higher than the portion of other grades.

Example 2

This example describes methods used to identify in a database of prostate cancer samples, those samples that are most similar to test prostate cancer samples. In this example, the database contained only prostate cancer samples and further included morphological information for each sample (see Table 3).

Morphologic Criteria

Nine criteria were selected to describe the structural properties of tissue: 1) Gland crowding 2) Gland roundness 3) Stromal reaction 4) Gleason score 5) Nuclear grade 6) Clefts 7) Lumen/gland ratio 8) Gland continuity 9) Cell separation. The details of the criteria are listed in Table 3. For each of the criteria, a tissue sample is assigned a score ranging from 0 to 2 or 3, except Gleason score which ranges from 6 to 10. Using the scores of the 9 morphologic criteria, the tissue morphologic similarity (TMS) was measured between tissue samples.

TABLE 3

Morphologic criteria to determine tissue similarity.

| Criteria | Description | Score 0 | Score 1 | Score 2 | Score 3 |
|---|---|---|---|---|---|
| Gland crowding | Gland tightness and cohesiveness | N/A | Sparse | Moderate | Very tight |
| Gland roundness | Roundness of external perimeter of gland | N/A | Very round | Moderate | Serrated contours or spindle shaped contours |
| Stromal reaction | Swollen, plump cells in stroma and splayed collagen fibers | N/A | No reaction | Little | |
| Gleason Score | Predominant and secondary Gleason score | — | — | — | — |
| Nuclear grade | Prominent nucleoli, variation in nuclear diameter and amount of chromatin | N/A | Normal | Some prominent nucleoli, moderate variation | Many prominent nucleoli, large variation |
| Clefts | Cleft formation or retraction artifact around cancer glands | N/A | <30% | ≥30% | — |
| Lumen/gland ratio | Ratio between lumen area and total gland area | N/A | Wide lumen | Moderate lumen | Tiny lumen |
| Gland continuity | Continuous sheets of cells | N/A | <30% | ≥30% | — |
| Cell separation | Individual cells separated by stroma | N/A | <10% | ≥10% | — |

Let TMS $(d_1,d_2)$ be the tissue morphologic similarity between two tissue samples $d_1$ and $d_2$ and computed as $TMS^i(d_1,d_2) = \Sigma_{i=1}^{9} TMS^i(d_1,d_2)$ where $TMS^i(d_1,d_2)$ is the morphologic tissue similarity for ith criteria. Assuming that tissue similarity between two samples with respect to a morphologic criterion is related to the number of samples between them as ordered by the score for the morphologic criterion, $TMS^i(d_1,d_2)$ is calculated as follows:

$$TMS^i(d_1, d_2) = \frac{\sum_{s=s^i_{d_1}+1}^{s^i_{d_2}-1} h^i(s) + \frac{1}{2}\left(h^i(s^i_{d_1}) + h^i(s^i_{d_2})\right)}{Z}$$

where $s_d^i$ is the ith morphologic criterion score of a tissue sample d, $h^i(s)$ is the number of samples having ith morphologic criterion score s, and Z is a normalization factor.

Morphological Feature Extraction

In prostate cancer, epithelial cells, which line 3D ducts in intact tissue, are of great interest. As cancer grows, epithelial cells grow (or invade) in and out of the glands in an uncontrolled way, and thus the structure of tissue, especially the local glandular structure, is distorted. The role of stroma cells, connective cells supporting epithelial cells, in cancer tissue has been recognized [24], [25]. To quantify the alterations in tissue morphology, the nuclear and cellular morphology of epithelial and stromal cells and lumens (empty space inside a gland) were examined. To quantify the nuclear and cellular morphology of epithelial and stromal cells and lumens, lumens and nuclei were segmented in tissue by considering their color intensities and geometric properties [23]. Due to lack of appreciable contrast, tissue samples were stained using hematoxyln and eosin (H&E) prior to segmentation. Segmentation can be conducted either on the stained image alone or with other imaging modalities [23], such as Fourier transform infrared (FT-IR) spectroscopy imaging [26] (which has been extensively validated in classifying histologic cell types in tissue [27], [28] and provides a color coded cell type image of tissue).

Using the segmented nuclei and lumens, a number of quantities measuring the morphologic changes in tissue are defined, and the quantities include the size, number, distance, spatial distribution, and shape of epithelial nuclei and lumens. The feature extraction process is described elsewhere [23]. In total, 26 quantities were defined. Detailed description of the quantities is discussed below under "Morphological Feature Extraction".

Computing average, standard deviation, sum total, minimum, and maximum of all or some of these quantities, 308 morphological features were extracted for each tissue sample (Table 4). The 308 features were obtained from the 26 feature categories as follows: one or more global and local features were computed such as average, standard deviation, total sum, etc. Local features were computed by using 5 different window sizes. For each window size, multiple features were computed (see discussion below).

TABLE 4

| Feature Name | Description | Type |
| --- | --- | --- |
| Size of epithelial cells | Number of pixels in epithelial cells. | $G_{TOT}$, $L_{MAX}$, $L_{STD}$ |
| Size of nucleus | Size of a nucleus. | $G_{AVG}$, $G_{TOT}$, $G_{STD}$, $L_{STD}$, $L_{STD,TOT}$, $L_{MAX,AVG}$, $L_{MAX,TOT}$ |
| Number of nuclei | Number of Nuclei. | $G_{TOT}$, $L_{STD}$, $L_{MAX,TOT}$ |
| Distance to lumen | Distance from the center of a nucleus to the boundary of the closest lumen. | $L_{AVG}$, $L_{STD}$, $L_{MAX,AVG}$, $L_{MIN,AVG}$ |
| Distance to epithelial cell boundary | Distance from center of the nucleus to the boundary of the epithelial cell. Epithelial cells are estimated by drawing a Voronois diagram of the nuclei. | $L_{AVG}$, $L_{STD}$, $L_{MAX,AVG}$, $L_{MIN,AVG}$ |
| Number of isolated nuclei | Number of nuclei without having a neighboring nucleus within a distance (<20 um) from the center of each nucleus. | $G_{TOT}$, $L_{STD}$, $L_{MAX,TOT}$ |
| Fraction of distant nuclei | Fraction of nuclei away from lumens (>30 um). | $G_{TOT}$ |
| Entropy of nuclei spatial distribution | $H(\text{Nuclei}) = -\sum_{i=1}^{n}\sum_{j=1}^{n} p(x_{ij}) \log p(x_{ij})$ where p( ) denotes the probability mass function of the number of nuclei in a partition, $x_{ij}$ denotes the number of nuclei in (i,j) the partition. | $G_{TOT}$, $L_{STD}$, $L_{MAX,TOT}$ |
| Size of lumen | Number of pixels in a lumen. | $G_{AVG}$, $G_{TOT}$, $G_{STD}$, $L_{MAX,AVG}$, $L_{MAX,TOT}$, $L_{STD,AVG}$, $L_{STD,TOT}$, $L_{MAX,AVG}^*$, $L_{MAX,TOT}^*$, $L_{STD,AVG}^*$, $L_{STD,TOT}^*$ |
| Number of lumen | Number of lumens. | $G_{TOT}$, $L_{MAX}$, $L_{STD}$ |
| Lumen roundness | $\dfrac{L_{peri}}{2L_{area}} r$ where $L_{peri}$ and $L_{area}$ are the perimeter and the size of a lumen, respectively, and r is the radius of a circle with the size of $L_{area}$. | $G_{AVG}$, $G_{STD}$, $L_{MAX,AVG}$, $L_{STD,AVG}$ |
| Lumen distortion | $\dfrac{STD(d_{Lcb})}{AVG(d_{Lcb})}$ where $d_{Lcb}$ is the distance from the center of a lumen to the boundary of a lumen. | $G_{AVG}$, $G_{STD}$, $L_{MAX,AVG}$, $L_{STD,AVG}$ |
| Lumen minimum bounding circle ratio | Ratio of the size of a minimum bounding circle of a lumen to the size of the lumen. | $G_{AVG}$, $G_{STD}$, $L_{MAX,AVG}$, $L_{STD,AVG}$ |
| Lumen convex hull ratio | Ratio of the size of a convex hull of a lumen to the size of the lumen. | $G_{AVG}$, $G_{STD}$, $L_{MAX,AVG}$, $L_{STD,AVG}$ |

TABLE 4-continued

| Feature Name | Description | Type |
|---|---|---|
| Lumen boundary symmetry | $\dfrac{\sum |L_{Ti} - L_{Bi}|}{\sum (L_{Ti} + L_{Bi})} + \dfrac{\sum |L_{Ri} - L_{Li}|}{\sum (L_{Ri} + L_{Li})}$ where $L_{Ti}$ and $L_{Bi}$ vertical distances from a vertical axis to the boundary of a lumen, $L_{Li}$, and $L_{Ri}$ are horizontal distances from a horizontal axis to the boundary of a lumen. | $G_{AVG}, G_{STD}, L_{MAX,AVG}, L_{STD,AVG}$ |
| Lumen area symmetry | $\dfrac{|L_{Larea} - L_{Rarea}|}{L_{Larea} + L_{Rarea}} + \dfrac{|L_{Tarea} - L_{Barea}|}{L_{Tarea} + L_{Barea}}$ where $L_{Larea}$, $L_{Rarea}$, $L_{Tarea}$, and $L_{Barea}$ are the size of left, right, top, and bottom quadrants, respectively. | $G_{AVG}, G_{STD}, L_{MAX,AVG}, L_{STD,AVG}$ |
| Spatial association of lumen and cytoplasm | $\dfrac{\eta_{adj}}{\eta_{adj} + \eta_{dis}}$ where $\eta_{dis}$ is a set of cytoplasm-rich pixels distant to lumens and $\eta_{adj}$ is a set of cytoplasm-rich pixels adjacent to lumens. | $G_{TOT}$ |
| Size of stromal cells | Number of pixels in stromal cells. | $G_{TOT}, L_{MAX}, L_{STD}$ |
| Minimum lumen distance | Minimum distance between lumens. | $G_{AVG}, G_{STD}, L_{AVG}, L_{STD}, L_{MAX,AVG}, L_{MIN,AVG}$ |
| Minimum gland distance | Minimum distance between glands. Fitting an ellipse to the neighboring nuclei $C_{sub}$ of a lumen gives an estimate of a gland. $C_{sub}$ is defined as any nucleus c satisfying Disatnce(c, l) ≤ AVG(Disatnce($C_{sub}$, l)) +m * STD(Disatnce($C_{sub}$, l)) where l is a lumen and Distance(c, l) denotes the distance from a nucleus c to a lumen l. m is set to 1.5, and, at each iteration, it is increased by 0.01 and nuclei which do not satisfy the criteria are eliminated. | $G_{AVG}, G_{STD}, L_{AVG}, L_{STD}, L_{MAX,AVG}, L_{MIN,AVG}$ |
| Ratio of lumen to epithelial cells | Ratio of the number of lumen pixels to the number of epithelial pixels in a tissue. | $G_{TOT}$ |
| Ratio of epithelial cells to stroma cells | Ratio of the number of epithelial pixels to the number of stroma pixels. | $G_{TOT}$ |
| Ratio of cell separation | Ratio of the number of separated epithelial nuclei to the total number of epithelial nuclei. Epithelial cells are designated as separated cells if their size <500 pixels and >90% of their boundary is adjacent to stroma cells. | $G_{TOT}$ |
| Ratio of sheets of cells | Ratio of the number of nuclei which neither are associated with any gland nor belong to separated cells to the total number of nuclei. | $G_{TOT}$ |
| Degree of cell dispersion | $\dfrac{\sigma^2}{\mu}$ where $\mu$ and $\sigma^2$ denote the average and the variance of the number of the pixels of a cell type, respectively. It is computed for both epithelial and stroma cells. | $L_{TOT}$ |
| Spatial autocorrelation of cells | Moran's I and Greary's C are computed. Moran's I of a cell type is computed as follows: $I = \dfrac{n}{\sum_i^n \sum_j^n w_{ij}} \dfrac{\sum_i^n \sum_j^n w_{ij}(y_i - \bar{y})(y_j - \bar{y})}{\sum_i^n (y_i - \bar{y})^2}$ where n is the number of the pixels labeled with the cell type, w is a weight associated with each pair of pixels, y is the number of adjacent pixels containing the same cell type, and $\bar{y}$ is AVG(y). Here, $w_{ij}$ is 1 if I i and j are adjacent and 0 otherwise. Greary's C is computed as follows: $C = \dfrac{n-1}{\sum_i^n \sum_j^n w_{ij}} \dfrac{\sum_i^n \sum_j^n w_{ij}(y_i - y_j)^2}{\sum_i^n (y_i - \bar{y})^2}$ | $G_{TOT}$ |

List of 308 features.
G and L denote global and local features, respectively. Local features were computed for 5 different window sizes.
AVG, TOT, STD, MAX and MIN represent average, sum total, standard deviation, maximum, and minimum of features in an entire sample or in a window.
*indicates that only a part of a lumen within a window is taken into account in computing feature values.

Morphological Feature Extraction

Previously, 17 quantities to describe structural properties of prostate tissue were defined and used to detect cancer tissue [23]. Eight are epithelium related features: 1) Size of epithelial cells 2) Size of a nucleus 3) Number of nuclei 4) Distance to lumen 5) Distance to epithelial cell boundary 6) Number of isolated nuclei 7) Fraction of distant nuclei 8) Entropy of nuclei spatial distribution. Nine are lumen-related features: 1) Size of a lumen 2) Number of lumens 3) Lumen roundness 4) lumen distortion 5) Lumen minimum bounding circle ratio 6) Lumen convex hull ratio 7) Symmetric index of lumen boundary 8) Symmetric index of lumen area 9) Spatial association of lumens and cytoplasm-rich regions.

Additionally, nine quantities describing characteristics of epithelium, stroma, lumens, and glands were added.

1) Number of stroma cells (number of stroma pixels in a tissue).

2) Minimum lumen distance (minimum distance between lumens).

3) Minimum gland distance (minimum distance between glands). To find glands in a tissue, first neighboring nuclei for each lumen are located. Neighboring nuclei to a lumen are the ones present within the epithelial cells next to the lumen. Then, a subset of the neighboring nuclei $C_{sub}$ are located which satisfy the following condition:

$$\forall c \in C_{sub}: \text{Distance}(c,l) \leq \text{AVG}(\text{Distance}(C_{sub},l)) + m*\text{STD}(\text{Distance}(C_{sub},l))$$

where l is a lumen, Distance (c,l) denotes the distance from a nucleus c to a lumen l, and AVG(•) and STD(•) indicates the average and standard deviation of •. Initially, m is set to 1.5. At each iteration, nuclei which do not satisfy the criteria are eliminated for further consideration and m is increased by 0.01. Fitting an ellipse to the subset of the neighboring nuclei gives an estimate of a gland for the lumen.

4) Ratio of lumen to epithelial cells (ratio of the number of lumen pixels to the number of epithelial pixels in a tissue).

5) Ratio of epithelial cells to stroma cells: (ratio of the number of epithelial pixels to the number of stroma pixels).

6) Ratio of cell separation (ratio of the number of separated epithelial nuclei to the total number of epithelial nuclei). Epithelial cells are designated as separated cells if their size <500 pixels and >90% of their boundary is next to stroma cells.

7) Ratio of sheets of cells (ratio of the number of nuclei which are not associated with any gland and do not belong to the separated cells to the total number of nuclei).

8) Degree of cell dispersion. Degree of dispersion of a cell type can be measured by variance-to-mean ratio (VMR)². It is defined as $$VMR = \frac{\sigma^2}{\mu}$$

where $\mu$ is the average number of the pixels labeled with a cell type and $\sigma^2$ is the variance of the number of the pixels labeled with the cell type. VMR is separately computed for epithelial and stroma cells.

9) Spatial autocorrelation of cells. To compute spatial autocorrelation of a cell type, two measures are adopted: Moran's I and Greary's C. Moran's I [29] can be computed as follows:

$$I = \frac{n}{\sum_i^n \sum_j^n w_{ij}} \frac{\sum_i^n \sum_j^n w_{ij}(y_i - \bar{y})(y_j - \bar{y})}{\sum_i^n (y_i - \bar{y})^2}$$

where n is the number of the pixels assigned to the cell type, w is a random variable representing a weight associated with each pair of the pixels, y is a random variable for the number of adjacent pixels containing the same cell type, $\bar{y}$ is the average of the number of adjacent pixels. For simplicity, $w_{ij}=1$ if i and j are adjacent and $w_{ij}=0$ otherwise. Similarly, Greary's C [30] can be calculated as follows:

$$C = \frac{n-1}{\sum_i^n \sum_j^n w_{ij}} \frac{\sum_i^n \sum_j^n w_{ij}(y_i - y_j)^2}{\sum_i^n (y_i - \bar{y})^2}.$$

Prior to compute spatial autocorrelation of a cell type, for each pixel, the number of the adjacent pixels labeled with the same cell type is computed. These counts are used to measure spatial autocorrelation. Both Moran's I and Greary's C are computed for epithelial cells and stroma cells, respectively.

For each of these 26 quantities, "global" and "local" features are measured. To compute, "global" features, AVG, STD, and sum total (TOT) of the quantities are used. "Local" features are calculated by sliding a rectangular window (N×N pixels) throughout a tissue sample. For each window, AVG and/or TOT of the quantities are computed, and then STD or MIN/MAX of the AVG and/or TOT values over all windows become "local" features. Five different sizes of the window (N=20, 60, 100, 140, 180) are applied, and the "local" features are computed for each.

Feature Selection

Feature selection is the step where the retrieval algorithm examines all available features (308 here) with respect to the training samples, and selects a subset to use on the test sample. This selection is generally based on the criterion of high accuracy on training data, but also strives to ensure generalizability beyond the training data. A two-stage feature selection approach was used. Size of a lumen, size of a nucleus, size of epithelial cells, and distance to lumen were the four most frequently selected feature categories.

In the first stage, the features are ordered by their individual retrieval performance, and sequentially, the retrieval performance of a feature set measured by adding a new feature at a time according to the order. In the second stage, feature selection continues with the feature set resulting the best performance in the first stage as the starting point, following the sequential floating forward selection (SFFS) method [31]. This method sequentially adds new features followed by conditional deletion(s) of already selected features. The retrieval capability of a feature set, required for feature selection, is measured by normalized discounted cumulative gain (NDCG) [32], a popular measure to evaluate ranking algorithms. Given a database D, and TMS scores, the performance of the retrieval function $f$ for a query q at rank position T is computed as:

$$NDCG(q, f; D, TMS) = \frac{\sum_{t=1}^{T} \frac{2^{TMS(q,r_t)} - 1}{\log_2(1 + t)}}{Z}$$

where $r_t$ indicates the tth closet sample to the query q, retrieved by the retrieval function $f$, from the database D, and Z denotes the normalization factor.

Tissue Matching

As a query is given, its morphological features are extracted and used to search for similar pre-examined samples in the database. To retrieve the most similar samples from the database, Ranking-SVM [33] was used, which sought to learn a function mapping onto a ranking (see below). That is, ranking-SVM provides a complete ranking of all samples in the database for the query. If a sample in the database is highly ranked to the query, then the query should be highly ranked for the sample. Regarding not only the ranking of the samples in the database to the test sample (query) but also the ranking of the query to the samples in the database, the ranking of a sample to the query is defined as:

$$\text{Ranking}(q,d_i;D) = \text{Ranking-SVM}(q,d_i;D) + \text{Ranking-SVM}(d_i,q;D\setminus d_i \cup q), i=1,\ldots,m$$

where Ranking-SVM (q, $d_i$; D) denotes the ranking of the sample $d_i$ to the query q determined by Ranking-SVM. Based on the ranking, top-T samples are retrieved. Since it is the sum of two rankings, it is likely that several rankings are tied. In such cases, the final ranking is determined by the ranking of the sample to the query, i.e., Ranking-SVM (q,$d_i$; D).

Ranking-SVM

Given a training dataset $\{(x_i, y_i)\}_{i=1}^{m}$ with a feature vector $x_i \in \Re^n$ and a (class) label $y_i \in \{-1,+1\}$, a classification support vector machine (SVM) learns a separating hyperplane which maximizes the margin between support vectors representing different classes. In Ranking SVM [33], a label $y_i$ denotes an ordering preference or a rank but a category, i.e., $\forall y_i \in \Re$ and a complete ranking can be made among the labels. It seeks to learn a function $f \in F$ satisfying the following relations for any pair of data points:

$$y_i > y_j \Leftrightarrow f(x_i) > f(x_j).$$

Constructing such function can be formulated as follows:

$$\min_{w,\xi_{ij} \geq 0} \frac{1}{2} w^T w + \frac{C}{|P|} \sum_{(i,j) \in P} \xi_{ij}$$

$$\text{s.t. } \forall (i,j) \in P : w^T(x_i - x_j) \geq 1 - \xi_{ij}$$

where C is a tradeoff between training error and model complexity and $\xi_{ij}$ is a slack variable. Intuitively, the function aims at minimizing the number of swapped pairs of training data points in terms of their desired rankings [33]. Interestingly, optimizing the formula is, in fact, equivalent to that of a classification SVM as pairwise difference vectors $(x_i - x_j)$ are provided.

In the disclosed methods, the label is given by a tissue similarity score between a pair of tissue samples, and a feature vector is generated by the difference vector between the feature vectors of the pair. In other words, a pair of tissue samples forms one instance to train Ranking-SVM, and it attempts to learn the ordering preference between the pairs of samples. Thus, as a query is given to the system, an instance for each pair of a query and a tissue sample in the database is generated, and the rankings of the entire instances are predicted by Ranking-SVM. The samples which result in the top-T ranking instances with the query are designated as most similar samples and provided with pathologists.

Balanced Training

The retrieval system was desired to provide only top-T closest samples, i.e., the rankings of high TMS scoring samples are of great interest in the new system. This issue is addressed by applying NDCG to measure the retrieval performance. Since Ranking-SVM tries to learn an overall ranking of the training dataset, biased or unbalanced training dataset may cause Ranking-SVM to be biased and its retrieval capability may be limited. To prevent this, roughly balanced sub-samples of the training dataset and trained Ranking-SVM on the sub-samples were used. To obtain the roughly balanced training dataset, the total TMS score range is divided into P equal-sized partitions. Then, $N_P$ number of pairs of samples from each partition was randomly selected. $N_P$ was set to the smallest number of pairs of samples in a partition.

Samples and Data Preparation

To demonstrate the utility of this method, 114 prostate cancer tissue samples were used. Both H&E stained and FT-IR images were available for the samples. H&E stained images were acquired on a standard optical microscope at 40× magnification, and the size of a pixel is 0.963 um×0.963 um. FT-IR images were acquired at a spatial pixel size of 6.25 um and a spectral resolution of 4 $cm^{-1}$ at an undersampling ratio of 2 using Perkin-Elmer Spotlight imaging system. Sample preparation and data acquisition for FT-IR imaging are described in [27]. Clinical information (Gleason grade, age, surgery type, etc.) of the samples were prepared by pathologic review, and 308 morphological features were extracted. The database generated contained 114 tissue images (of two different modalities), their clinical information, and 308 morphological features.

Results

Tissue Morphologic Similarity Measure

For the 114 prostate cancer samples, a pathologist scored each using the nine morphologic criteria in Table 3. The pathologist was blind to the previous diagnosis and clinical information of the samples. Provided with the scores for the nine morphologic criteria, tissue morphologic similarity (TMS) was measured for all possible pairs of 114 tissue samples. The TMS scores were used to train the retrieval algorithm, Ranking-SVM.

Figure 17:
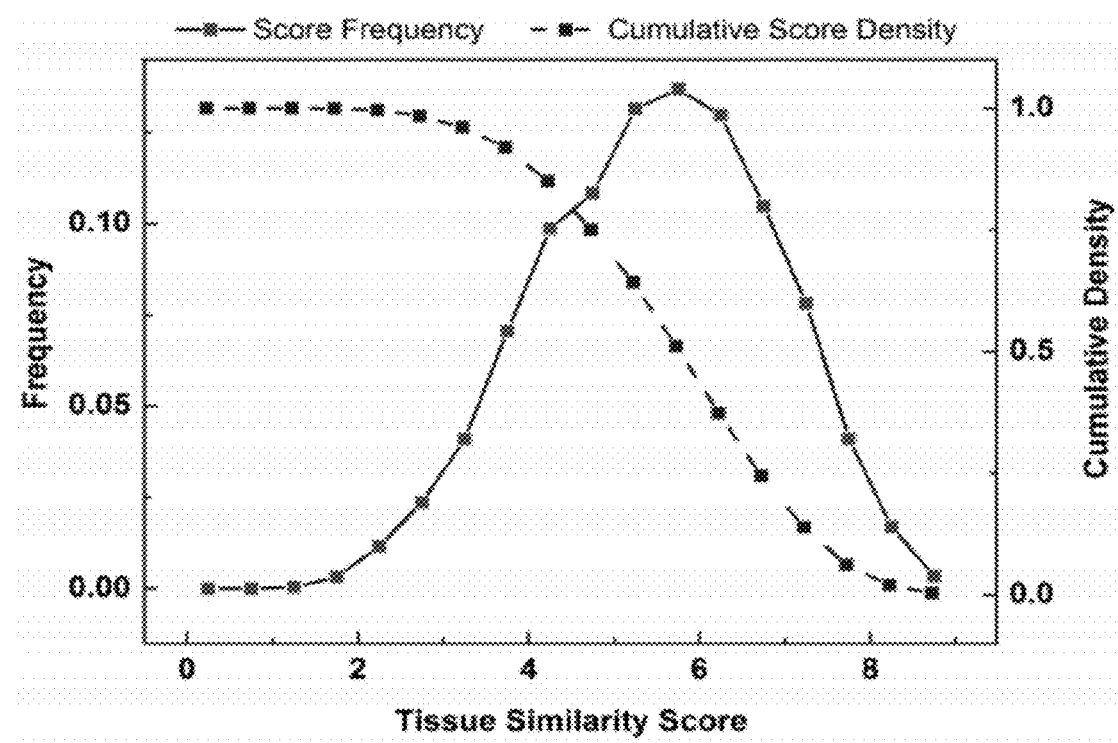
FIG. 17 is a graph showing the frequency and cumulative density of similarity scores. Mid-range scores (5~6) are mostly dominant, and high scoring (≥8) samples were rare.

The TMS score was not evenly distributed, and mid-range score (5~6) was dominant. Only a few sample pairs had a high TMS score, e.g., ~2% of samples pairs had scores ≥8 (FIG. 17).

Evaluation of Tissue Retrieval System

To evaluate the tissue retrieval system, K-fold cross-validation was performed (K=10). The entire dataset was divided into K roughly equal-sized partitions, one partition was left out as "test data" (or queries), the union of the remaining K−1 partitions (the "training data") was used to build the database where T similar samples are retrieved for each query (T=5). This was repeated K times with different choices of the left-out partition. In each repetition, the 2-stage feature selection was carried out on the training data via L-fold cross-validation (L=5). The average NDCG at rank position T of the tissue retrievals for the queries, across all K repetitions, was computed to measure the performance of the retrieval. To handle the imbalance of TMS scores in the dataset, roughly balanced training dataset was formed by dividing the entire score range into P partitions (P=10) and randomly taking equal number of samples from each partition.

Performance of Tissue Retrieval System

To examine the retrieval performance, a threshold similarity score $th_s$ was changed from 0 to 8, and designated a sample as a good match to a query if their similarity score is $\geq th_s$. Then, the number of queries provided with $N_G$ or more good matches ($N_G=1, \ldots, T$) was counted.

Figure 18A:
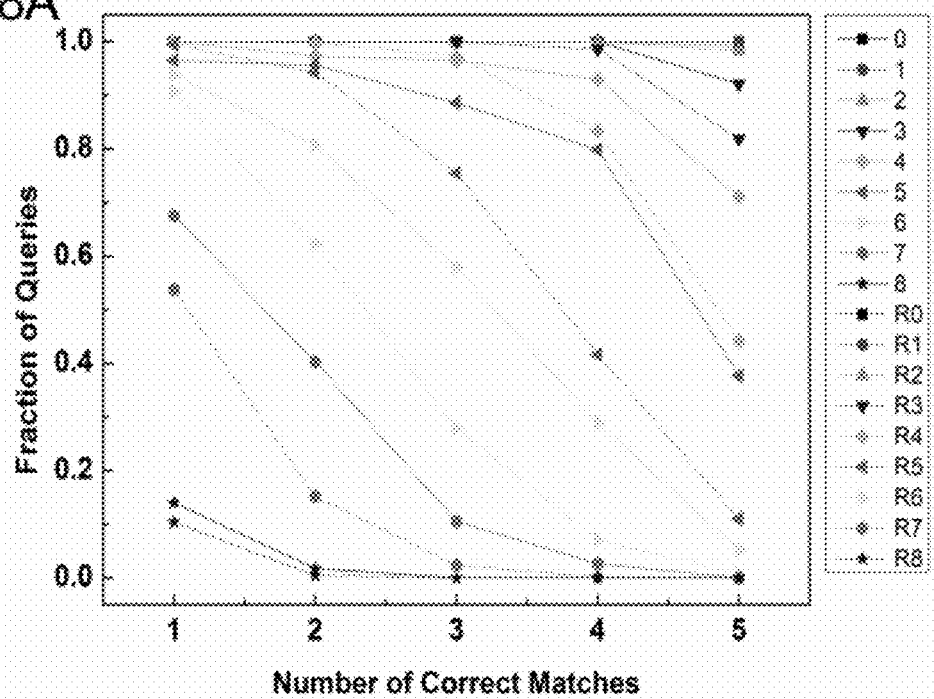
FIGS. 18A and B are graphs showing the queries retrieving good matching cases. (A) The number of queries retrieving at least $N_G$ number of good matches, out of T retrieved samples, is computed ($N_G$=1, ..., T), and compared to the random chance (R0~R9) of retrieving that number of good matching cases. (B) The frequency and cumulative density of similarity scores are plotted for the entire training samples and T matching samples, respectively. A good matching case is defined as a pair of samples whose similarity score is ≥$th_s$, $th_s$=0, ..., 8. Random chance of retrieving ≥$N_G$ good matching cases is computed as $$Pr(X \geq N_G) = \sum\nolimits_{x \geq N_G} \frac{\binom{N_{SS}}{x}\binom{N_S - N_{SS}}{T-x}}{\binom{m}{T}}$$
Figure 18B:
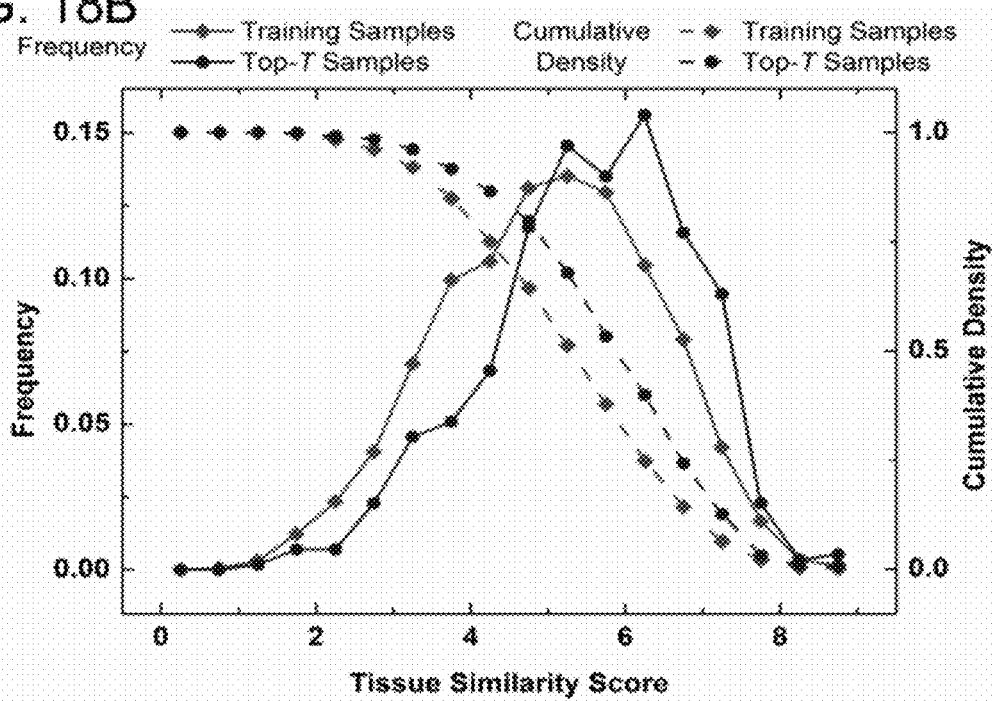

As shown in FIG. 18A, ~80% and ~60% of the queries retrieved ≥4 and ≥3 good matching cases when setting $th_s$ to 5 and 6, respectively. Compared to the random chance of retrieving ≥4 and ≥3 good matches, both were increased by more than two-fold, and the retrievals were statistically significant (p-value <1.0e-10) (Table 5). As shown in FIG. 18B, t TMS scores of pairs of the query and its T matching samples are higher than those of pairs of the query and all the samples in the database, especially TMS scores of 6 or greater.

TABLE 5

Statistical significance of tissue retrieval*

| | | $th_s$ | | |
|---|---|---|---|---|
| | | 5 | 6 | 7 |
| $N_G$ | 3 | 101 | 66 | 12 |
| | | <0.001 | <1.e-10 | <0.0001 |
| | 4 | 91 | 33 | 3 |
| | | <1.e-16 | <1.e-11 | <0.01 |
| | 5 | 43 | 6 | 0 |
| | | <1.e-12 | <0.001 | 1 |

*The number of queries ($N_q$) retrieving at least $N_G$ number of good matching cases as a good match is defined as TMS ≥ $th_s$ and its statistical significance. Assuming the number of good matches follows a binomial distribution, p-value is computed as $$\Pr(X \geq N_q) = \sum_{x \geq N_q} \binom{m}{x} p^x (1-p)^{m-x}$$

where p is a random chance of retrieving ≥ $N_G$ good matches (TMS ≥ $th_s$). (Top) the number of queries and (bottom) its statistical significance.

FIG. 19 shows examples of queries and their matching cases. A pair of samples belonging to the same grade tends to have a high TMS score, but high TMS scoring sample pairs are not necessarily the same grade. These types of samples would not be retrieved if the method was built solely using Gleason grade. Moreover, as the Ranking-SVM was trained on the entire training dataset (i.e., without balanced training), fewer samples having higher TMS scores with the query were retrieved (FIGS. 20A and 20B), for example, TMS score ≥6. Accordingly, using a roughly balanced subset of the training dataset is a valid decision and provides an effective and robust retrieval process.

Although only the five closest samples to a query were retrieved from the database, one will recognize that more or fewer samples can be retrieved. The more samples retrieved, the greater the likelihood that good matching cases will be provided to a pathologist. However, retrieving many samples (e.g., >10) could be a burden to pathologists due to additional time and effort to decide what samples are relevant and useful. Hence, providing a few, but the most similar samples could be most helpful and effective. It necessitates little time and work for pathologists to make a diagnosis based on the retrieved samples, but delivers good matches. The disclosed methods can be designed to retrieve greater or fewer samples from the database. Moreover, if one or more morphological properties are of greater interest to a pathologist, the similarity score can be re-computed and used to train the retrieval system. Therefore, the system is potentially, highly adaptable to users' demand and purpose.

In summary, provided herein is a time- and cost-effective information management and decision-making system for cancer pathology. The system includes a database that allows pathologists to easily manage and maintain the previous cases and outcomes, and immediate access to them is available due to efficient retrieval algorithm. Accordingly, the performance of tissue retrieval is reliant on both database and matching algorithm.

REFERENCES

[1] Montironi, et al., "Gleason grading of prostate cancer in needle biopsies or radical prostatectomy specimens: contemporary approach, current clinical significance and sources of pathology discrepancies," Bju International, 95:1146-1152, 2005.

[2] Cintra and Billis, "Histologic grading of prostatic adenocarcinoma: intraobserver reproducibility of the Mostofi, Gleason and Bocking grading systems," Int Urol Nephrol, 23: 449-54, 1991.

[3] Ozdamar, et al., "Intraobserver and interobserver reproducibility of WHO and Gleason histologic grading systems in prostatic adenocarcinomas," Int Urol Nephrol, 28:73-7, 1996.

[4] Egevad, et al., "Current practice of Gleason grading among genitourinary pathologists," Human Pathology, 36: 5-9, 2005.

[5] Stotzka, et al., "A Hybrid Neural and Statistical Classifier System for Histopathologic Grading of Prostatic Lesions," Analytical and Quantitative Cytology and Histology, 17:204-218, 1995.

[6] Wetzel, et al., "Evaluation of prostate tumor grades by content-based image retrieval," Washington, D.C., USA, 1999, pp. 244-252.

[7] Smith, et al., "Similarity measurement method for the classification of architecturally differentiated images," Computers and Biomedical Research, 32:1-12, 1999.

[8] Jafari-Khouzani and Soltanian-Zadeh, "Multiwavelet grading of pathological images of prostate," Ieee Transactions on Biomedical Engineering, 50:697-704, 2003.

[9] Farjam, et al., "Tree-structured grading of pathological images of prostate," in Proc SPIE Int Symp Med Imag, San Diego, Calif., 2005, pp. 840-851.

[10] Farjam, et al., "An image analysis approach for automatic malignancy determination of prostate pathological images," Cytometry Part B: Clinical Cytometry, 72B:227-240, 2007.

[11] Doyle, et al., "AUTOMATED GRADING OF PROSTATE CANCER USING ARCHITECTURAL AND TEXTURAL IMAGE FEATURES," in Biomedical Imaging: From Nano to Macro, 2007. ISBI 2007. 4th IEEE International Symposium on, 2007, pp. 1284-1287.

[12] Metaxas, et al. (eds.), "Gland Segmentation and Computerized Gleason Grading of Prostate Histology by Integrating Low-, High-level and Domain Specific Information," in Proceedings of 2nd Workshop on Microsopic Image Analysis with Applications in Biology, Piscataway, N.J., USA, 2007.

[13] Tabesh, et al., "Multifeature prostate cancer diagnosis and Gleason grading of histological images," Ieee Transactions on Medical Imaging, 26:1366-78, 2007.

[14] Huang and Lee, "Automatic Classification for Pathological Prostate Images Based on Fractal Analysis," Ieee Transactions on Medical Imaging, 28:1037-50, 2009.

[15] Mericsko R J, (ed). Evaluation of prostate tumor grades by content-based image retrieval. 1999: SPIE.

[16] Classification of potential nuclei in prostate histology images using shape manifold learning. Proceedings of the Machine Vision, 2007. ICMV 2007. International Conference on 28-29 Dec. 2007.

[17] Jafari-Khouzani K, Soltanian-Zadeh H. Multiwavelet grading of pathological images of prostate. Ieee Transactions on Biomedical Engineering 2003; 50(6):697-704.

[18] Tree-structured grading of pathological images of prostate. Proceedings of the Proc SPIE Int Symp Med Imag, 2005.

[19] Schulte E K W. Standardization of Biological Dyes and Stains—Pitfalls and Possibilities. *Histochemistry* 95(4):319-28, 1991.

[20] Sved P D, Gomez P, Manoharan M, Kim S S, Soloway M S. Limitations of biopsy Gleason grade: Implications for counseling patients with biopsy Gleason score 6 prostate cancer. *J Urology* 172(1):98-102, 2004.

[21] Harnden P, Shelley M D, Coles B, Staffurth J, Mason M D. Should the Gleason grading system for prostate cancer be modified to account for high-grade tertiary components? A systematic review and meta-analysis. *Lancet Oncology* 8(5):411-9, 2007.

[22] Shah R B. Current Perspectives on the Gleason Grading of Prostate Cancer. *Archives of Pathology & Laboratory Medicine* 133(11):1810-6, 2009.

[23] Kwak J, Hewitt S, Sinha S, Bhargava R. Multimodal microscopy for automated histologic analysis of prostate cancer. *BMC Cancer* 2011; 11(1):62.

[24] Ayala G, Tuxhorn J A, Wheeler T M, et al. Reactive stroma as a predictor of biochemical-free recurrence in prostate cancer. *Clin Cancer Res* 2003; 9(13):4792-801.

[25] Cordon-Cardo C, Kotsianti A, Verbel D A, et al. Improved prediction of prostate cancer recurrence through systems pathology. *J Clin Invest* 2007; 117(7):1876-83.

[26] Colarusso P, Kidder L H, Levin I W, et al. Infrared spectroscopic imaging: From planetary to cellular systems. *Applied Spectroscopy* 1998; 52(3):106a-20a.

[27] Fernandez D C, Bhargava R, Hewitt S M, Levin I W. Infrared spectroscopic imaging for histopathologic recognition. *Nature Biotechnology* 2005; 23(4):469-74.

[28] Bhargava R, Fernandez D C, Hewitt S M, Levin I W. High throughput assessment of cells and tissues: Bayesian classification of spectral metrics from infrared vibrational spectroscopic imaging data. *Biochimica Et Biophysica Acta-Biomembranes* 2006; 1758(7):830-45.

[29] Moran P A. Notes on continuous stochastic phenomena. *Biometrika* 1950; 37(1-2):17-23.

[30] Geary R C. The Contiguity Ratio and Statistical Mapping. *The Incorporated Statistician* 1954; 5(3):115-46.

[31] Pudil P, Novovicova J, Kittler J. Floating Search Methods in Feature-Selection. *Pattern Recogn Lett* 1994; 15(11):1119-25.

[32] Jarvelin K, Kekalainen J. IR evaluation methods for retrieving highly relevant documents. *IR evaluation methods for retrieving highly relevant documents* 2000:41-8.

[33] Training linear SVMs in linear time. *Proceedings of the Proceedings of the 12th ACM SIGKDD international conference on Knowledge discovery and data mining* 2006: ACM.

In view of the many possible embodiments to which the principles of the disclosure can be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:

1. A method comprising:
   obtaining, by a processor, a Hematoxylin and Eosin (HE) stained image of a test prostate sample;
   obtaining, by the processor, an Infrared (IR) image of the test prostate sample;
   performing segmentation, by the processor, for the test prostate sample utilizing the HE stained image and the IR image;
   identifying, by the processor, epithelial cells, epithelial nuclei and lumens in the test prostate sample according to the segmentation;
   selecting, by the processor, a group of morphological features from a plurality of morphological features associated with the epithelial cells, the epithelial nuclei and the lumens of the test prostate sample;
   determining the group of morphological features for the epithelial cells, the epithelial nuclei and the lumens in the test prostate sample based on an analysis of at least the HE stained image;
   performing, by the processor, a comparison of the group of morphological features for the test prostate sample with reference sample information stored in a database, wherein the reference sample information represents reference morphological features for reference prostate samples, wherein the reference prostate samples are identified in the database by a confirmed pathological status;
   selecting, by the processor, a group of reference prostate samples from the reference prostate samples according to the comparison; and
   presenting, by the processor, reference data for the group of reference prostate samples.

2. The method of claim 1, wherein the IR image is generated using Fourier transform IR imaging.

3. The method of claim 1, wherein the test prostate sample is a human sample, and wherein the plurality of morphological features comprise size of epithelial cells, size of a nucleus, number of nuclei, distance to lumen, distance to epithelial cell boundary, number of isolated nuclei, fraction of distant nuclei, entropy of nuclei spatial distribution, size of a lumen, number of lumens, lumen roundness, lumen distortion, lumen minimum bounding circle ratio, lumen convex hull ratio, symmetric index of lumen boundary, symmetric index of lumen area, spatial association of lumens and cytoplasm-rich regions, number of stroma cells, minimum lumen distance, minimum gland distance, ratio of lumen to epithelial cells, ratio of epithelial cells to stroma cells, ratio of cell separation, ratio of sheets of cells, degree of cell dispersion and spatial autocorrelation of cells, or any combination thereof.

4. The method of claim 1, wherein the selecting of the group of morphological features comprises:
   selecting a subset of morphological features from the plurality of morphological features, wherein the determining of the group of morphological features for the epithelial cells, the epithelial nuclei and the lumens in the test prostate sample includes analyzing at least the HE stained image according to the subset;
   determining an additional morphological feature that is least redundant with the subset and that is correlated with a class label for the test prostate sample;
   adjusting the subset to include the additional morphological feature to generate an adjusted subset; and
   repeating the determining of the group of morphological features for the epithelial cells, the epithelial nuclei and the lumens in the test prostate sample by analyzing the at least the HE stained image according to the adjusted subset, wherein the additional morphological feature is utilized as a starting point for the analyzing.

5. The method of claim 1, wherein the presenting of the reference data for the group of reference prostate samples includes presenting images at a display device coupled with the processor.

6. The method of claim 1, wherein the selected group of reference prostate samples have a most similar k value to the test prostate sample according to a k-nearest neighbor analysis.

7. The method of claim 1, wherein the segmentation is based on color intensities and geometric properties determined from the HE stained image and the IR image.

8. The method of claim 1, wherein the reference prostate samples of the database comprises a plurality of Gleason grade 2, 3, 4, and 5 cancer samples, benign prostatic hyperplasia (BPH) samples, normal prostate samples, or combinations thereof.

9. The method of claim 1, wherein the selecting of the group of morphological features from the plurality of morphological features includes utilizing a minimum-redundancy-maximal-relevance (mRMR) criterion.

10. The method of claim 9, wherein the selecting of the group of morphological features from the plurality of morphological features further includes utilizing a sequential floating forward selection process.

11. The method of claim 1, further comprising:
receiving, by the processor, user input indicating accuracy information associated with the reference data for the group of reference prostate samples.

12. The method of claim 11, wherein the accuracy information is utilized for adjusting information in the database.

13. The method of claim 1, further comprising:
adjusting, by the processor, accuracy data utilized in selecting a subsequent group of morphological features from the plurality of morphological features associated with epithelial cells, epithelial nuclei and lumens of a subsequent test prostate sample, wherein the adjusting of the accuracy data is based on user feedback.

14. The method of claim 1, further comprising:
identifying, by the processor, stroma cells according to the segmentation.

15. The method of claim 1, wherein the selecting of the group of morphological features comprises:
selecting a subset of morphological features from the plurality of morphological features, wherein the determining of the group of morphological features for the epithelial cells, the epithelial nuclei and the lumens in the test prostate sample includes analyzing at least the HE stained image according to the subset;
determining an accuracy associated with the subset utilized for determining the group of morphological features;
identifying an inaccurate morphological feature according to the determining of the accuracy;
adjusting the subset to remove the inaccurate morphological feature to generate an adjusted subset; and
repeating the determining of the group of morphological features for the epithelial cells, the epithelial nuclei and the lumens in the test prostate sample by analyzing the at least the HE stained image according to the adjusted subset.

16. The method of claim 1, wherein the performing of the segmentation for the test prostate sample comprises overlaying the HE stained image and the IR image for image registration.

17. The method of claim 1, wherein the selecting of the group of morphological features comprises selecting the group according to accuracy information stored in the database and adjusting the group to add or remove morphological features according to accuracy determinations associated with iterations of the performing of the comparison of the group of morphological features with the reference sample information stored in the database.

18. A database device comprising:
a memory that stores executable instructions; and
a processor coupled with the memory, wherein the processor, responsive to executing the instructions, performs operations comprising:
storing reference sample information in the memory, wherein the reference sample information represents reference morphological features for reference prostate samples, wherein the reference prostate samples are identified in the database by a confirmed pathological status as prostate cancer tissue samples, normal prostate tissue samples, and benign prostatic hyperplasia tissue samples, wherein the reference sample information includes accuracy data associated with utilizing particular morphological features for sample matching;
providing reference data for a group of reference prostate samples selected from the reference prostate samples according to a comparison of a group of morphological features for a test prostate sample with the reference sample information stored in the memory, wherein selecting of the group of reference prostate samples is based on a segmentation for the test prostate sample utilizing a Hematoxylin and Eosin (HE) stained image and an Infrared (IR) image of the test prostate sample, wherein the segmentation identifies epithelial cells, epithelial nuclei and lumens in the test prostate sample;
receiving user input indicating accuracy information associated with the reference data for the group of reference prostate samples; and
adjusting the accuracy data to generate adjusted accuracy data that is utilized in selecting a subsequent group of morphological features from a plurality of morphological features during an analysis of a subsequent test prostate sample.

19. A computer-readable storage device comprising instructions which, responsive to being executed by a processor, cause the processor to perform operations comprising:
obtaining a Hematoxylin and Eosin (HE) stained image of a test prostate sample;
obtaining an Infrared (IR) image of the test prostate sample;
performing segmentation for the test prostate sample utilizing the HE stained image and the IR image;
identifying epithelial cells, epithelial nuclei and lumens in the test prostate sample according to the segmentation;
selecting a group of morphological features from a plurality of morphological features associated with the epithelial cells, the epithelial nuclei and the lumens of the test prostate sample;
determining the group of morphological features for the epithelial cells, the epithelial nuclei and the lumens in the test prostate sample based on an analysis of at least the HE stained image;
performing a comparison of the group of morphological features for the test prostate sample with reference sample information stored in a database, wherein the reference sample information represents reference morphological features for reference prostate samples, wherein the reference prostate samples are identified in the database by a confirmed pathological status;
selecting a group of reference prostate samples from the reference prostate samples according to the comparison; and
presenting reference data for the group of reference prostate samples.

20. The computer-readable storage device of claim 19, wherein the IR image is generated using Fourier transform IR imaging.

* * * * *